United States Patent
Kamiyama et al.

(10) Patent No.: US 11,994,481 B2
(45) Date of Patent: May 28, 2024

(54) CONCENTRATION MEASUREMENT DEVICE

(71) Applicant: OMRON Corporation, Kyoto (JP)

(72) Inventors: Susumu Kamiyama, Kyoto (JP); Hajime Kano, Kyoto (JP); Shinya Nakagawa, Kyoto (JP); Hideyuki Nakao, Kyoto (JP); Kenichi Handa, Kyoto (JP); Takashi Kasai, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 354 days.

(21) Appl. No.: 17/434,963

(22) PCT Filed: Mar. 17, 2020

(86) PCT No.: PCT/JP2020/011702
§ 371 (c)(1),
(2) Date: Aug. 30, 2021

(87) PCT Pub. No.: WO2020/189677
PCT Pub. Date: Sep. 24, 2020

(65) Prior Publication Data
US 2022/0136988 A1    May 5, 2022

(30) Foreign Application Priority Data
Mar. 19, 2019  (JP) .................................. 2019-051263

(51) Int. Cl.
*G01N 25/18* (2006.01)
*G01N 27/18* (2006.01)

(52) U.S. Cl.
CPC ............. *G01N 25/18* (2013.01); *G01N 27/18* (2013.01)

(58) Field of Classification Search
CPC .... G01N 25/18; G01N 27/18; G01N 33/0004; G01N 33/225
See application file for complete search history.

(56) References Cited

U.S. PATENT DOCUMENTS

| | | | |
|---|---|---|---|
| 4,902,138 A | 2/1990 | Goeldner et al. | |
| 9,068,871 B2 * | 6/2015 | Yamamoto | .............. G01F 1/688 |

(Continued)

FOREIGN PATENT DOCUMENTS

| | | |
|---|---|---|
| CN | 88101718 A | 10/1988 |
| CN | 105229451 A | 1/2016 |

(Continued)

OTHER PUBLICATIONS

International Search Report issued in International Application No. PCT/JP2020/011702 dated Jun. 23, 2020. English translation provided.

(Continued)

*Primary Examiner* — Freddie Kirkland, III
(74) *Attorney, Agent, or Firm* — ROSSI, KIMMS & McDOWELL LLP

(57) ABSTRACT

It is possible to reduce a decrease in accuracy of measuring the concentration of a measurement target gas even in a case where, in a mixture of gases, there is a gas greatly different from another gas in a rate of change in thermal conductivity with respect to temperature. The concentration measurement (Continued)

device includes a sensor configured to measure the concentration of a measurement target gas in a mixture of gases on the basis of thermal conductivity of the measurement target gas, the mixture of gases including two or more components, and a heating unit configured to heat the mixture of gases so that the concentration of the measurement target gas can be uniquely determined with respect to the thermal conductivity.

4 Claims, 23 Drawing Sheets

(56) References Cited

U.S. PATENT DOCUMENTS

| | | | | |
|---|---|---|---|---|
| 9,140,659 | B2 * | 9/2015 | De Coulon | G01N 33/0004 |
| 9,739,739 | B2 * | 8/2017 | De Coulon | G01N 33/0006 |
| 9,921,588 | B2 * | 3/2018 | Hornung | G01F 1/74 |
| 10,232,303 | B2 * | 3/2019 | Van Der Sluis | G01N 25/4873 |
| 11,525,722 | B2 * | 12/2022 | Yamamoto | G01F 1/6888 |
| 2013/0081445 | A1 | 4/2013 | De Coulon | |
| 2014/0069205 | A1 | 3/2014 | Yamamoto | |
| 2015/0338361 | A1 | 11/2015 | De Coulon | |
| 2016/0103082 | A1 | 4/2016 | Kimura | |
| 2016/0161951 | A1 | 6/2016 | Hornung | |
| 2016/0310887 | A1 | 10/2016 | Van Der Sluis | |
| 2020/0400474 | A1 | 12/2020 | Yamamoto | |

FOREIGN PATENT DOCUMENTS

| | | |
|---|---|---|
| EP | 0698786 A1 | 2/1996 |
| JP | H07113777 A | 5/1995 |
| JP | 2002136595 A | 5/2002 |
| JP | 2004286492 A | 10/2004 |
| JP | 2013076699 A | 4/2013 |
| JP | 2014132232 A | 7/2014 |
| JP | 5652315 B2 | 1/2015 |
| JP | 2017502904 A | 1/2017 |
| JP | 6435389 B2 | 12/2018 |
| JP | 2019144085 A | 8/2019 |

OTHER PUBLICATIONS

Written Opinion issued in International Application No. PCT/JP2020/011702 dated Jun. 23, 2020. English translation provided.

Office Action issued in Chinese Appln. No. 202080017860.X dated Jan. 10, 2024. English translation provided.

* cited by examiner

CONCENTRATION MEASUREMENT DEVICE

TECHNICAL FIELD

The present invention relates to a concentration measurement device.

BACKGROUND ART

A flow sensor is utilized to detect a flow rate or flow direction of fluid. The flow sensor includes, for example, a sensor having a heater on a thin film (a membrane) and thermopiles arranged so as to sandwich the heater. In a flow sensor including such a sensor, when a heat distribution generated by the heater heating the thin film is disturbed by a flow of fluid, the disturbance is measured as a difference in thermoelectric power generated in the thermopile.

For example, Patent Document 1 discloses a flow sensor formed integrally with a flow path through which fluid passes. Patent Literature 2 discloses a flow sensor that is formed separately from a flow path and has a sensor exposed to outside, the sensor detecting a flow rate.

PRIOR ART DOCUMENTS

Patent Documents

Patent Document 1: Japanese Unexamined Patent Publication No. 5652315
Patent Document 2: Japanese Unexamined Patent Publication No. 6435389

SUMMARY OF THE INVENTION

Problems to be Solved by the Invention

The inventors of the present invention have found a possibility of application of a flow sensor to a concentration measurement of a measurement target gas in a mixture of gases, and verified measurement accuracy thereof. Gas that is not a mixture of gases (that is, a gas of one kind of substance) has thermal conductivity that varies linearly with respect to temperature. However, a problem has been found as a result of the verification that desired measurement accuracy can be obtained in a case where a rate of change in thermal conductivity with respect to temperature is substantially equal among gases in a mixture of gases, while concentration measurement accuracy is low in a case where, in a mixture of gases, there is a gas greatly different from another gas in a rate of change in thermal conductivity with respect to temperature. Furthermore, in the verification, it has been also found that, in order to measure thermal conductivity of a gas by using a thermopile and a heater, it is not necessary to use a plurality of thermopiles and one thermopile placed near the heater is sufficient.

An object of an aspect of the disclosed technology is to provide a concentration measurement device capable of reducing a decrease in accuracy of measuring a concentration of a measurement target gas even in a case where, in a mixture of gases, there is a gas greatly different from another gas in a rate of change in thermal conductivity with respect to temperature.

Means for Solving the Problem

An aspect of the disclosed technology is exemplified by the following concentration measurement device. The concentration measurement device includes a sensor configured to measure a concentration of a measurement target gas in a mixture of gases on the basis of thermal conductivity of the measurement target gas, the mixture of gases including two or more components, and a heating unit configured to heat the mixture of gases so that a concentration of the measurement target gas can be uniquely determined with respect to the thermal conductivity.

A mixture of gases is a gas including two or more components. Examples of a mixture of gases include a fuel gas such as city gas or liquefied petroleum gas (LP gas), air, and the like. The measurement target gas may be a gas including only one component or a gas including two or more components. Instead of thermal conductivity, the sensor may use thermal resistivity that is reciprocal of thermal conductivity. In a mixture of gases including a gas greatly different from another gas in a rate of change in thermal conductivity with respect to temperature, there is a range in which a relation between thermal conductivity and a concentration is not on a one-to-one basis (for example, a range in which two concentrations correspond to one thermal conductivity) depending on temperature of air. Such a range is generated, for example, in a case where the mixture of gases is at a low temperature. In the disclosed technology, a heating unit heats a mixture of gases so that a concentration of the measurement target gas can be uniquely determined with respect to thermal conductivity, whereby it is possible to reduce a decrease in accuracy of measuring a concentration of the measurement target gas even in a case where, in the mixture of gases, there is a gas greatly different from another gas in a rate of change in thermal conductivity with respect to temperature.

The disclosed technology may have the following characteristics. The sensor includes a pair of thermoelectromotive devices in which electromotive force according to temperature is generated and a heating unit that is placed between the pair of thermoelectromotive devices and generates heat according to an applied voltage. The sensor measures a flow rate of the mixture of gases according to the electromotive force generated in the pair of thermoelectromotive devices heated by the heating unit, and further includes a controller configured to control a voltage applied to the heating unit. The controller applies, to the heating unit, a second voltage higher than a first voltage that is applied when measuring a flow rate of the mixture of gases, and causes the sensor to measure a concentration of the mixture of gases.

The thermoelectromotive device is, for example, a thermopile. The thermopile outputs thermoelectric power according to ambient temperature. The heating unit is, for example, a heater that generates heat according to the applied voltage. The heating unit is placed near the thermoelectromotive device. The concentration measurement device has a characteristic in which a heating unit is placed between a pair of thermoelectromotive devices, and therefore can be used as a flow sensor that measures a flow rate or flow velocity of fluid. The concentration measurement device measures a concentration of the measurement target gas on the basis of electromotive force generated by the thermoelectromotive device. Note that measurement of a concentration of a measurement target gas is only required to be based on electromotive force generated in either one thermoelectromotive device of the pair of thermoelectromotive devices. For example, a rate of change in thermal conductivity with respect to temperature is greatly different between argon mixed oxygen and nitrogen. In a mixture of gases including gases greatly different from each other in a rate of change in thermal conductivity with respect to temperature, there is a range in which a relation between electromotive force generated in a thermoelectromotive device and a concentration is not on a one-to-one basis (for example, a range in which two concentrations correspond to one electromotive force) depending on temperature of the mixture of gases. Such a range is generated, for example, in a case where the mixture of gases is at a low temperature. In the concentration measurement device, a voltage applied to the heating unit when the concentration of the measurement target gas is measured is the second voltage that is higher than the first voltage. Application of the second voltage to the heating unit increases temperature of air around the heating unit and causes a relation between electromotive force generated in either one thermoelectromotive device of a pair of thermoelectromotive devices and a concentration to be on a one-to-one basis. Therefore, the concentration measurement device can reduce a decrease in accuracy of measuring a concentration of the measurement target gas even in a case where, in a mixture of gases, there is a gas greatly different from another gas in a rate of change in thermal conductivity with respect to temperature.

The disclosed technology may have the following characteristics. The concentration measurement device further includes a thermometer configured to measure temperature of the mixture of gases, in which the controller stores, for each temperature of the mixture of gases, a correspondence between a range in which a concentration of the mixture of gases can be uniquely determined on the basis of electromotive force generated in the thermoelectromotive device and a voltage applied to the heating unit, and the controller acquires temperature of the mixture of gases measured by the thermometer and determines the second voltage by referring to the correspondence on the basis of the acquired temperature. With such a characteristic, the concentration measurement device can suitably control the second voltage for each temperature of the mixture of gases.

The disclosed technology may have the following characteristics. The concentration measurement device is applied to a concentrator configured to generate a concentrated gas in which concentrations of two or more predetermined components in air are increased, in which the mixture of gases is a concentrated gas concentrated by the concentrator, and the measurement target gas is a gas including the two or more predetermined components included in the concentrated gas.

The air is, for example, a mixture of gases including nitrogen, oxygen, and argon. The concentration measurement device can measure a concentration of a gas including two or more predetermined components in the concentrated gas concentrated by the concentrator. For example, in a case where the two or more predetermined components are oxygen and argon, the concentration measurement device can measure a concentration of the measurement target gas including oxygen and argon in gas concentrated by the concentrator.

The disclosed technology may have the following characteristics. The concentrator removes nitrogen from air including nitrogen, oxygen, and argon to generate a concentrated gas in which a concentration of oxygen and argon is increased, the predetermined component includes oxygen and argon, and the sensor is provided on a flow path through which the concentrator supplies the concentrated gas. With such a characteristic, the concentration measurement device can measure a concentration of a mixture of gases (a mixture of gases including oxygen and argon) in concentrated gas concentrated by the concentrator. That is, the concentration measurement device can confirm whether or not the concentrator can concentrate oxygen to a desired concentration.

Effect of the Invention

The concentration measurement device can reduce a decrease in accuracy of measuring a concentration of a measurement target gas even in a case where, in a mixture of gases, there is a gas greatly different from another gas in a rate of change in thermal conductivity with respect to temperature.

MODE FOR CARRYING OUT THE INVENTION

Embodiment

Hereinafter, a flow sensor according to an embodiment will be described with reference to the drawings. In the embodiment, there will be described a case where a flow sensor, which detects a flow rate or flow velocity of fluid, is applied to an oxygen concentrator. The oxygen concentrator removes (reduces) nitrogen from air including nitrogen, oxygen, and a trace amount of argon, thereby generating a concentrated gas having a higher oxygen concentration than air does. Being generated by removing nitrogen from air, the concentrated gas is a mixture of gases including oxygen, a trace amount of argon, and nitrogen not removed by the oxygen concentrator. Hereinafter, in the description herein, a mixture of gases including oxygen and a trace amount of argon is referred to as argon mixed oxygen. The flow sensor according to the embodiment measures, for example, a concentration of argon mixed oxygen in a concentrated gas. Oxygen and argon are examples of "predetermined components".

Figure 1:
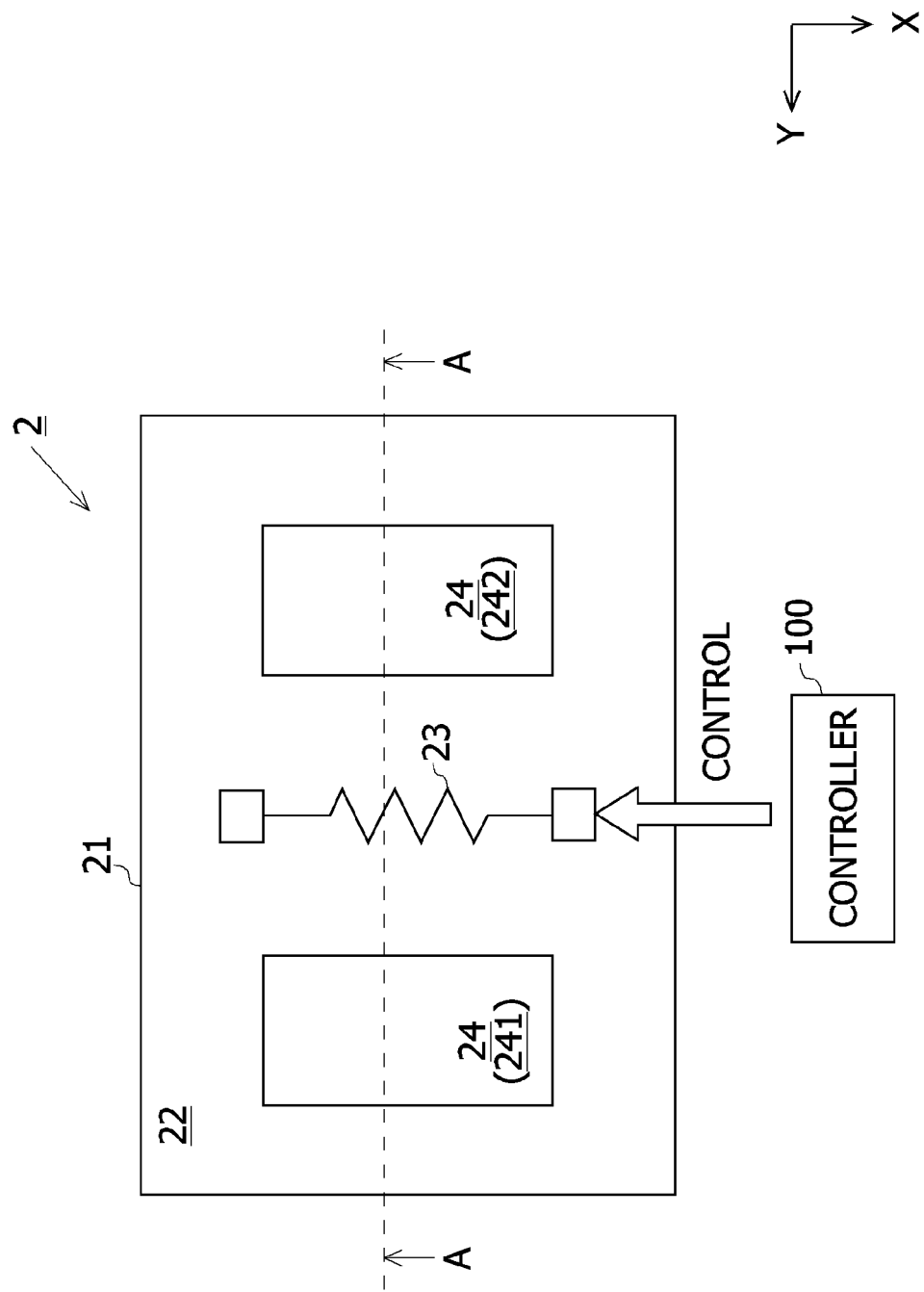
FIG. 1 is a top view of a flow sensor according to an embodiment.
Figure 2:
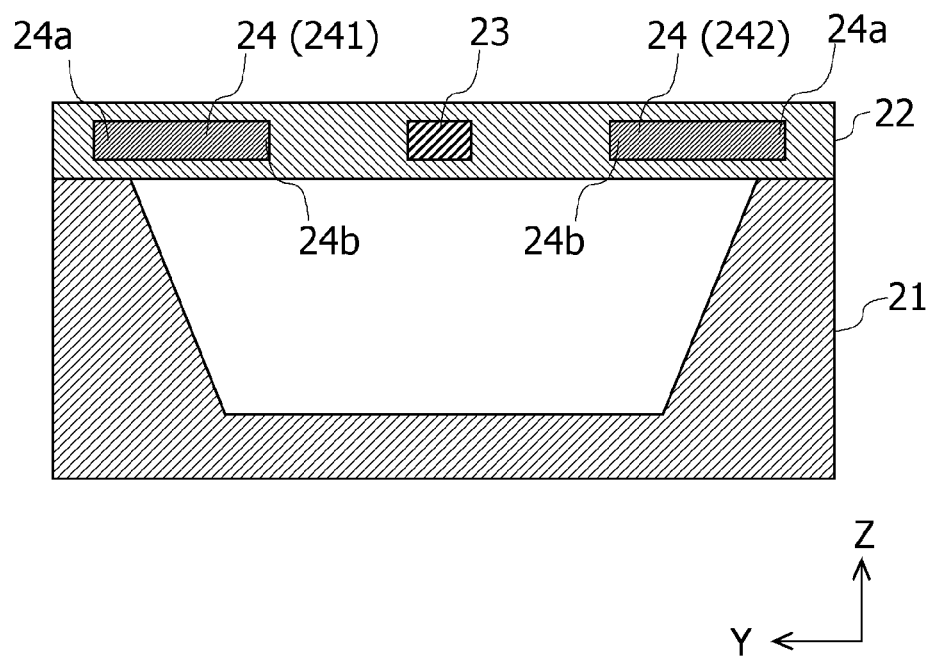
FIG. 2 is a cross-sectional view taken along the line A-A in FIG. 1.

FIG. 1 is a top view of the flow sensor according to the embodiment, and FIG. 2 is a cross-sectional view taken along the line A-A in FIG. 1. Hereinafter, in the description herein, a side close to a main body 21 is a lower side, and a side close to a membrane 22 is an upper side. A flow sensor 2 exemplified in FIG. 1 includes the main body 21 and the membrane 22. In the membrane 22, a heater 23 and thermopiles 24, 24 are arranged in a line. In the description herein, a direction in which the heater 23 and the thermopiles 24, 24 are arranged in a line is also referred to as a Y direction, a direction orthogonal to the Y direction is also referred to as an X direction, and a vertical direction (thickness direction) is also referred to as a Z direction.

The flow sensor 2 is a sensor that measures a flow velocity or a flow rate of fluid (For example, gas). The flow sensor 2 includes the main body 21 and the membrane 22. The main body 21 has a hollow shape with an open upper surface (a mortar shape), and a material thereof is, for example, silicon. As exemplified in FIG. 2, the membrane 22 is thin film that closes an opening of the main body 21 at an upper edge of the main body 21. The membrane 22 is provided with the heater 23 and the thermopiles 24, 24. The heater 23 and the thermopiles 24, 24 are arranged in a line along the Y direction. When the thermopiles 24, 24 are distinguished from each other, one of the thermopiles 24, 24 is referred to as a thermopile 241, and another of the thermopiles 24, 24 is referred to as a thermopile 242. The flow sensor 2 is an example of a "concentration measurement device".

The heater 23 is a heating apparatus that heats the membrane 22. Each of the thermopiles 24, 24 is a thermocouple that generates thermoelectric power by receiving heat from the membrane 22. One end 24a of each of the thermopiles 24, 24 in a width direction (Y direction) is placed on the main body 21, and another end 24b is placed, on the membrane 22, near the heater 23 (on a hollow-shaped region of the main body 21). The one end 24a of a thermopile 24 is, for example, a cold junction, and the another end 24b is a hot junction. Each of the thermopiles 24, 24 outputs, as thermoelectric power, a temperature difference between the cold junction (one end 24a) and the hot junction (another end 24b). At the cold junction, temperature is maintained substantially constant by the cold junction being placed on the main body 21. At the hot junction, heat from the heater 23 is easily received via the membrane 22 by the hot junction being placed near the heater 23. As the temperature difference increases, higher thermoelectric power is generated. Furthermore, in a case where both the thermopiles 24, 24 have the same temperature, the thermopiles 24, 24 generate equal thermoelectric power. The flow sensor 2 is, for example, a thermal flow sensor that heats the membrane 22 by using the heater 23 and measures a flow velocity or a flow rate on the basis of a difference in thermoelectric power between the thermopiles 24, 24, the difference being generated by a difference in a heat distribution in the membrane 22. The flow sensor 2 is manufactured by, for example, Micro Electro Mechanical Systems (MEMS). The flow sensor 2 is, for example, a surface-mount type flow sensor in which the membrane 22 provided with the heater 23 and the thermopiles 24, 24 is exposed to outside. The heater 23 is an example of a "heating unit". The thermopile 24 is an example of a "thermoelectromotive device". The flow sensor 2 is an example of a "sensor".

Figure 3:
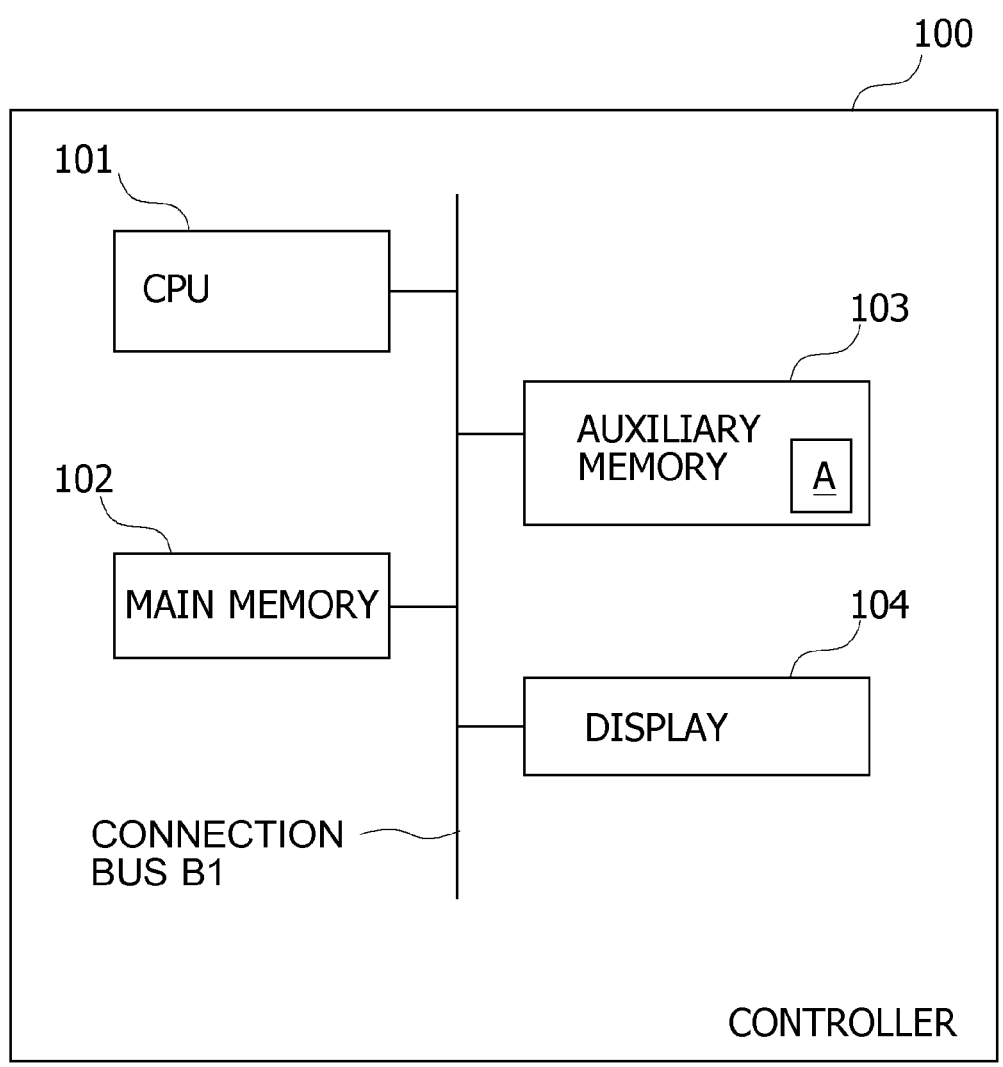
FIG. 3 is a diagram illustrating an example of a hardware configuration of a controller.

A controller 100 controls an amount of heat generated by the heater 23 by controlling a voltage applied to the heater 23. For example, when measuring a concentration of argon mixed oxygen, the controller 100 applies, to the heater 23, a second voltage higher than a first voltage that is applied to the heater 23 when measuring flow (a flow rate or flow velocity) of fluid. The controller 100 is, for example, an information processor including a processor or a memory. FIG. 3 is a diagram illustrating an example of a hardware configuration of a controller. The controller 100 includes a central processing unit (CPU) 101, a main memory 102, an auxiliary memory 103, a display 104, and a connection bus B1. The CPU 101, the main memory 102, the auxiliary memory 103, and the display 104 are mutually connected by the connection bus B1.

The CPU 101 is not limited to a single processor, and may have a multiprocessor configuration. The CPU 101 may be a combination of a processor and an integrated circuit exemplified by a microcontroller unit (MCU), a system on a chip (SoC), a system LSI, a chip set, or the like.

The main memory 102 and the auxiliary memory 103 are recording media that can be read by the controller 100. The main memory 102 is exemplified as a memory directly accessed from the CPU 101. The main memory 102 includes a random access memory (RAM) and a read only memory (ROM).

The auxiliary memory 103 is a nonvolatile memory exemplified by, for example, an erasable programmable ROM (EPROM), a solid state drive (Solid State Drive, SSD), a hard disk drive (Hard Disk Drive, HDD), or the like. The auxiliary memory 103 stores a program A for controlling a voltage applied to the heater 23 or various parameters used for measuring a concentration of argon mixed oxygen.

In the controller 100, the CPU 101 loads the program A, which is stored in the auxiliary memory 103, on a work area of the main memory 102, and controls a voltage applied to the heater 23 or measures a concentration of argon mixed oxygen through execution of a program. The controller 100 is an example of a "controller".

The display 104 displays, for example, data processed by the CPU 101 or data stored in the main memory 102. Examples of the display include a display device such as a cathode ray tube (CRT) display, a liquid crystal display (LCD), a plasma display panel (PDP), an electroluminescence (EL) panel, or an organic EL panel.

Figure 4:
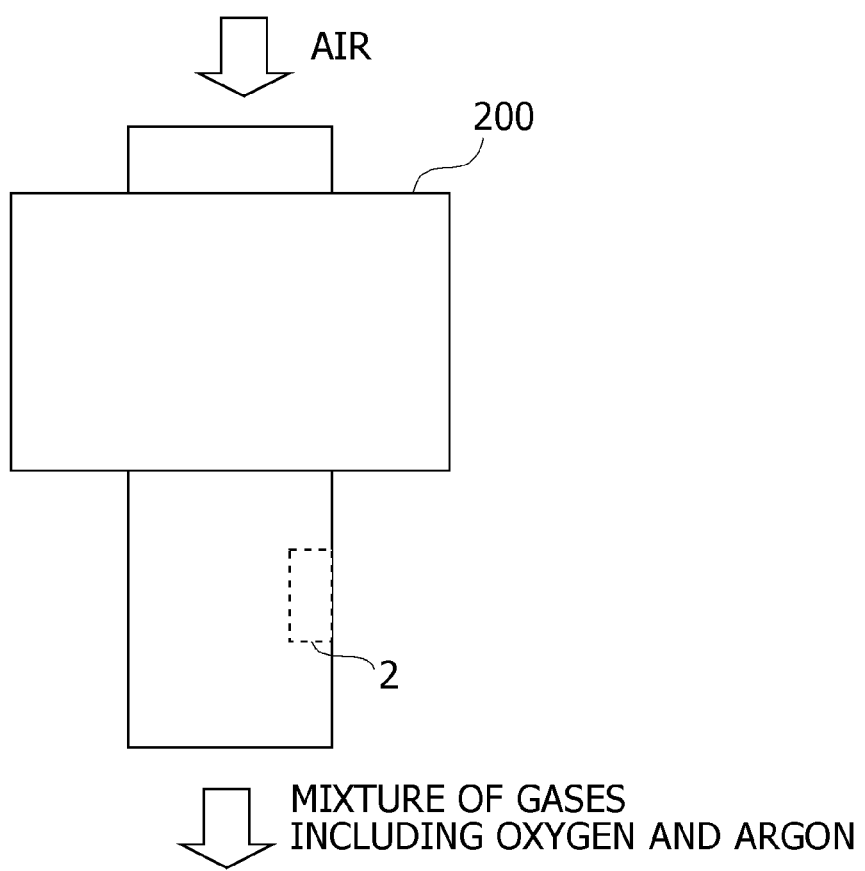
FIG. 4 is a diagram illustrating an example of a case where the flow sensor according to the embodiment is applied to an oxygen concentrator.

FIG. 4 is a diagram illustrating an example of a case where the flow sensor according to the embodiment is applied to the oxygen concentrator. By removing nitrogen from air supplied from outside, an oxygen concentrator 200 generates a concentrated gas for which oxygen is concentrated. The flow sensor 2 is provided, for example, inside a flow path through which the oxygen concentrator 200 supplies a concentrated gas obtained by concentrating oxygen, thereby measuring a concentration of argon mixed oxygen in the concentrated gas generated by the oxygen concentrator.

Figure 5:
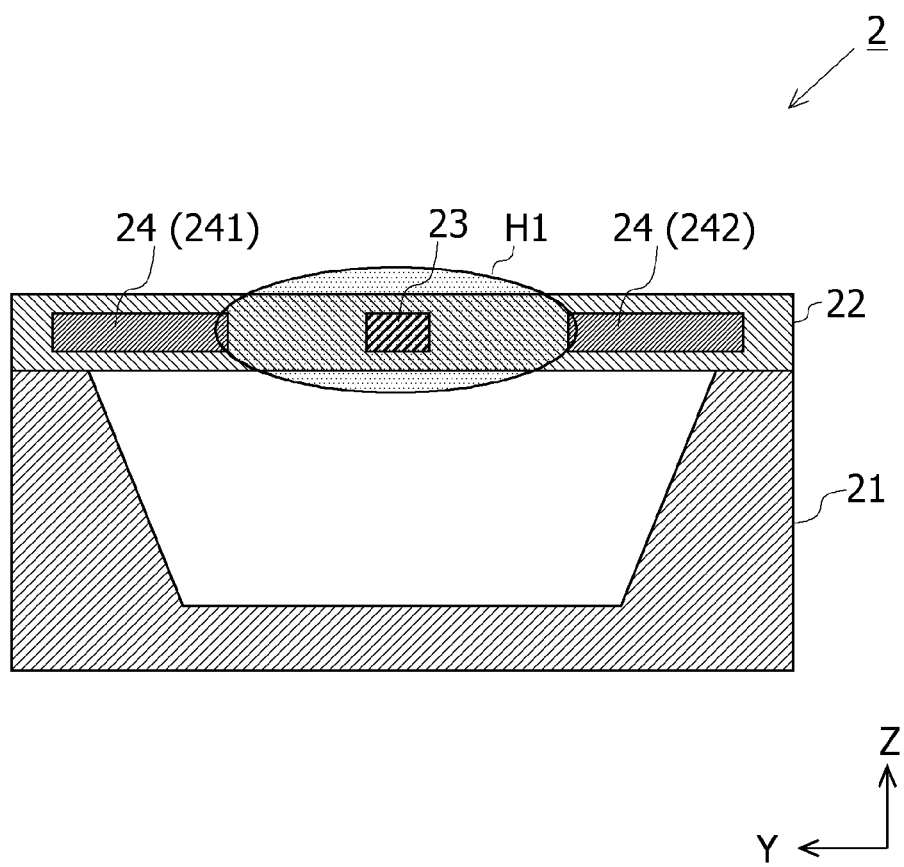
FIG. 5 is a first diagram schematically illustrating a method for measuring a flow rate by the flow sensor.
Figure 6:
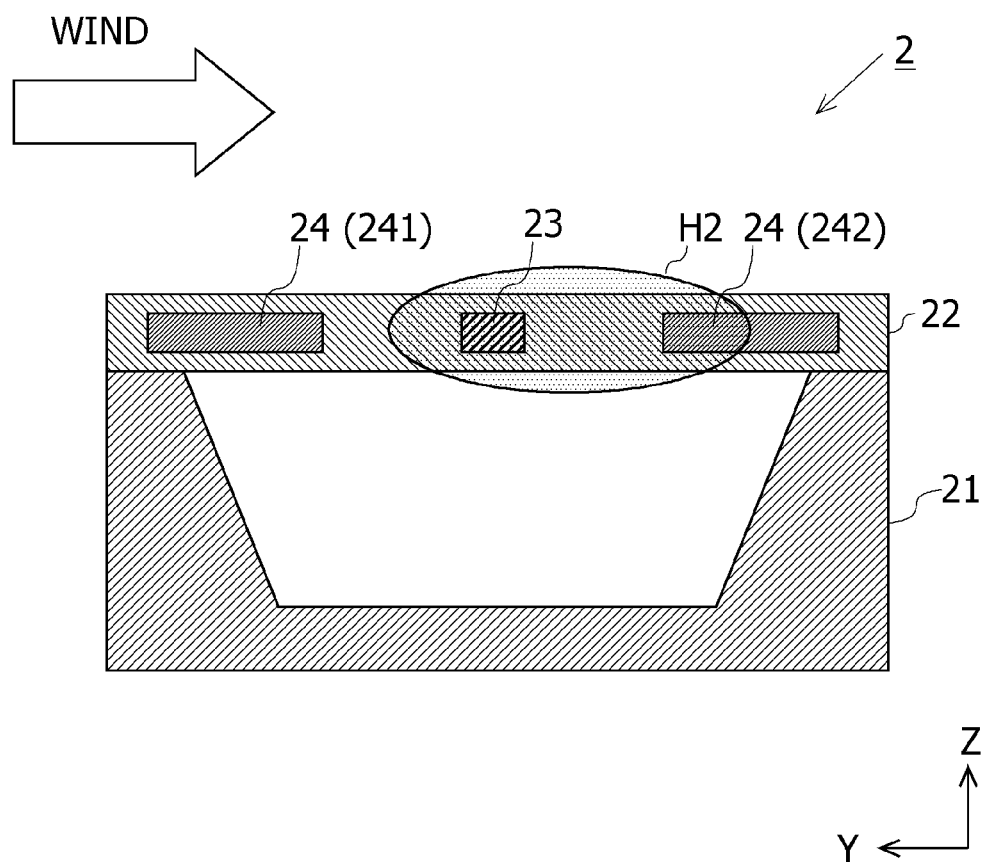
FIG. 6 is a second diagram schematically illustrating a method for measuring a flow rate by the flow sensor.

FIGS. 5 and 6 are diagrams schematically illustrating a method for measuring a flow rate by the flow sensor. FIG. 5 exemplifies a state where no wind is blowing around the flow sensor 2. In a case where no wind is blowing around the flow sensor 2, the farther a position is from the heater 23, the lower temperature the position has, and as exemplified by a heat distribution H1, a heat distribution in the membrane 22 is uniform centered on the heater 23. Therefore, both the thermopiles 24, 24 are heated to the same temperature by the heater 23, and temperatures detected by the thermopiles 24, 24 are equal.

FIG. 6 exemplifies a state where wind is blowing around the flow sensor 2. Assuming that one of the thermopiles 24, 24 is the thermopile 241 and another of the thermopiles 24, 24 is the thermopile 242, FIG. 6 exemplifies a state in which wind is blowing from the thermopile 241 toward the thermopile 242. An upstream side of the wind is cooled by the wind, and temperature of the upstream side decreases. Therefore, as exemplified by a heat distribution H2, the heat distribution in the membrane 22 shifts to a downstream side rather than the upstream side of the heater 23 (the downstream side becomes hotter than the upstream side). Therefore, a temperature difference detected by the thermopile 242 positioned at the downstream side of the heater 23 is higher than a temperature difference detected by the thermopile 241 positioned at the upstream side of the heater 23. As a result, there is generated a difference between a temperature difference $T_1$ detected by the thermopile 241 and a temperature difference $T_2$ detected by the thermopile 242. Therefore, by measuring a difference $\Delta T_1$ between the temperature difference $T_1$ detected by the thermopile 241 and the temperature difference $T_2$ detected by the thermopile 242 (that is, $T_2-T_1$), the flow sensor 2 can detect a direction of the wind and detect strength of the wind.

In a case where $\Delta T_1$ is positive, the temperature difference $T_2$ detected by the thermopile 242 is larger than the temperature difference $T_1$ detected by the thermopile 241. Therefore, the flow sensor 2 can detect that the wind is blowing in a direction from the thermopile 241 toward the thermopile 242. Furthermore, in a case where $\Delta T_1$ is negative, the temperature difference $T_1$ detected by the thermopile 241 is larger than the temperature difference $T_2$ detected by the thermopile 242. Therefore, the flow sensor 2 can detect that the wind is blowing in a direction from the thermopile 242 toward the thermopile 241. Further, in a case where $\Delta T_1$ is 0 (zero), both the thermopiles 24, 24 detect the same temperature difference. Therefore, the flow sensor 2 can detect that no wind is blowing (or blowing wind is weaker than a lower limit of a detection range). Furthermore, the larger an absolute value of $\Delta T_1$ is, the stronger wind the flow sensor 2 detects.

Figure 7:
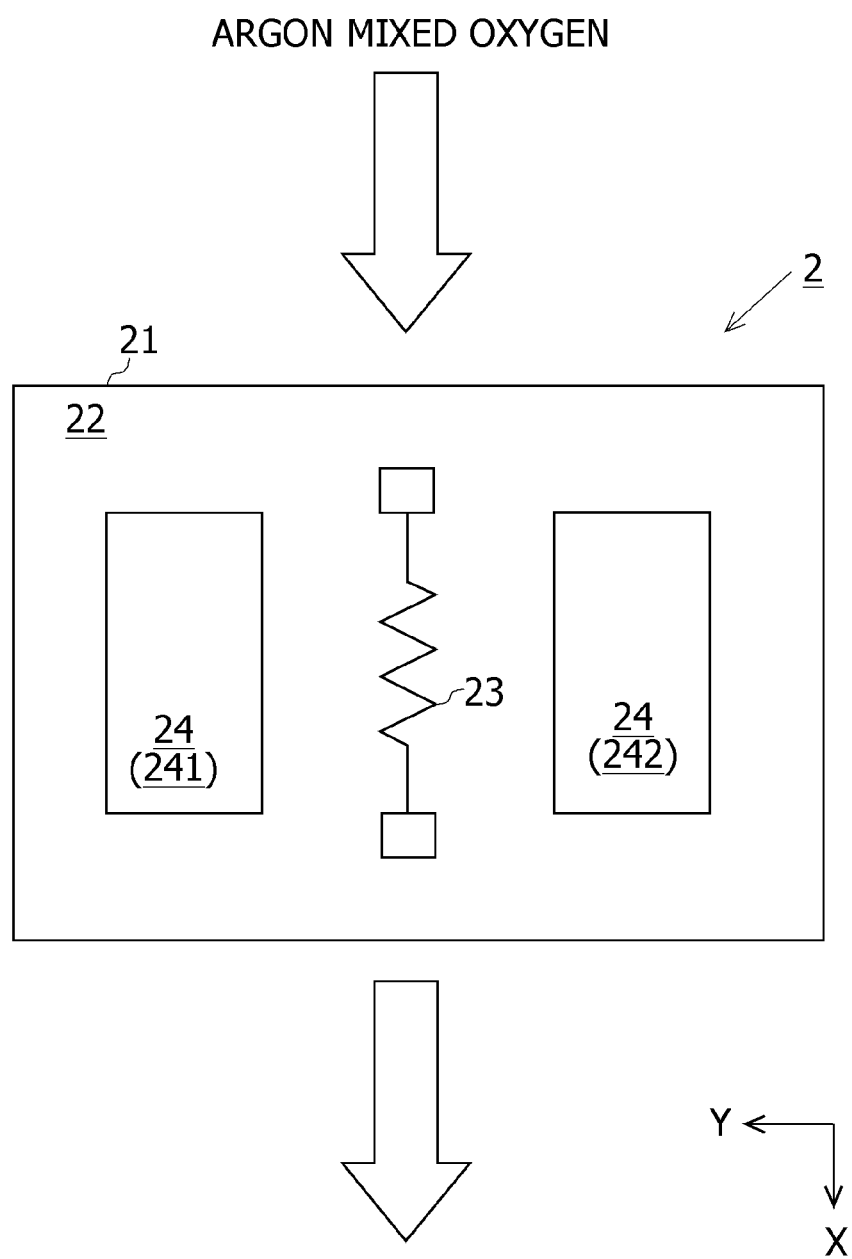
FIG. 7 is a diagram schematically illustrating a flow of argon mixed oxygen of a case where the flow sensor according to the embodiment is applied to measurement of a concentration of argon mixed oxygen.

In a case where the flow sensor 2 is used to measure a flow rate, the flow sensor 2 is placed such that wind flows in the Y direction as exemplified in FIG. 6 described above. Meanwhile, in a case where the flow sensor 2 is used to measure a concentration of argon mixed oxygen, wind is blown in a direction different from the direction of wind exemplified in FIG. 6. FIG. 7 is a diagram schematically illustrating a flow of argon mixed oxygen of a case where the flow sensor according to the embodiment is applied to measurement of a concentration of argon mixed oxygen. FIG. 7 is a top view of the flow sensor 2. As exemplified in FIG. 7, in a case where the concentration of argon mixed oxygen is measured, the flow sensor 2 is placed such that the argon mixed oxygen flows in the X direction orthogonal to a direction in which the heater 23 and the thermopile 24 are arranged in a line (Y direction). Here, in order to increase measurement accuracy of the concentration measurement, it is preferable to set the flow velocity of argon mixed oxygen to be as low as possible (almost windless).

Figure 8:
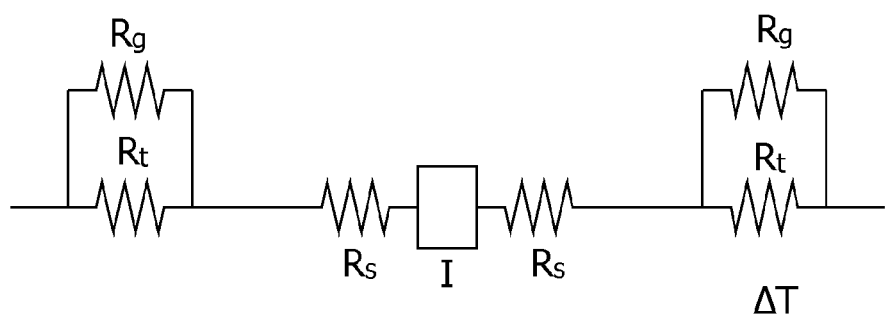
FIG. 8 is a diagram schematically exemplifying a thermal equivalent circuit of the flow sensor according to the embodiment.

FIG. 8 is a diagram schematically exemplifying a thermal equivalent circuit of the flow sensor according to the embodiment. In FIG. 8, I represents thermal resistance of the heater 23, $R_t$ represents thermal resistance of a thermopile, and $R_g$ represents thermal resistance of a concentrated gas. Furthermore, $\Delta T$ represents a temperature difference $\Delta T$ detected by a thermopile 24 (that is, either the thermopile 241 or the thermopile 242) when no wind is blowing. $\Delta T$ can be determined, for example, by the following.

[Mathematical formula 1]

$$\Delta T = \frac{I}{2} \frac{1}{\frac{1}{R_t} + \frac{1}{R_g}} \quad \text{(Mathematical formula 1)}$$

In the above (Mathematical formula 1), $R_t$ and I are known. Therefore, $R_g$, which is thermal resistance of a concentrated gas, can be determined by the flow sensor 2 measuring $\Delta T$. The auxiliary memory 103 stores a correspondence between the thermoelectric power of the thermopile 24 and $\Delta T$, a correspondence between voltage applied to the heater 23 and an amount of heat generated by the heater 23, the above (Mathematical formula 1), and thermal resistance $R_t$ of the thermopile. The correspondence between the thermoelectric power and $\Delta T$, and the correspondence between voltage applied to the heater 23 and an amount of heat generated by the heater 23 are, for example, a table, a mathematical formula, or the like.

(Relation Between Thermal Conductivity and Mixture Ratio of Gases)

Figure 9:
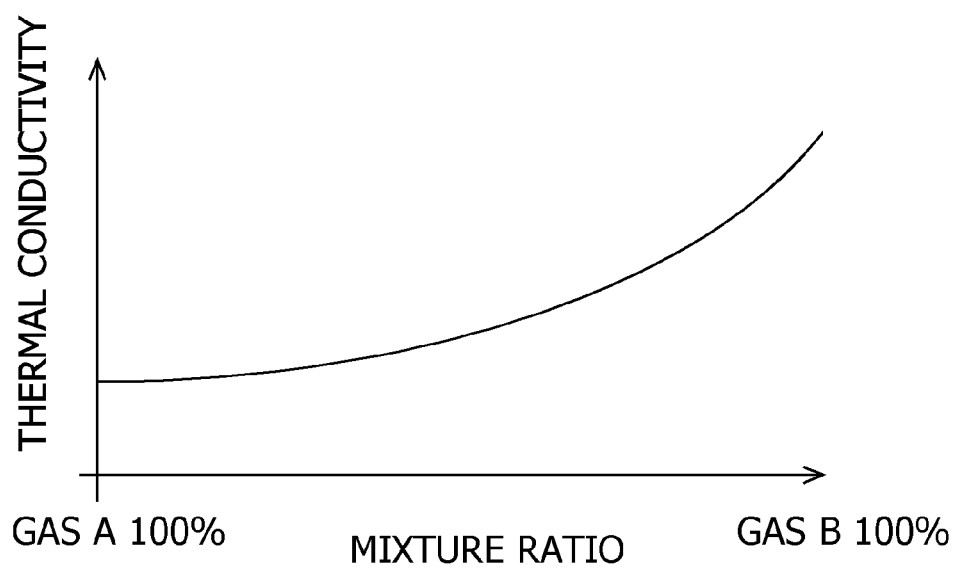
FIG. 9 is a diagram exemplifying a relation between thermal conductivity of a mixture of gases and a mixture ratio of gases in the mixture of gases.

FIG. 9 is a diagram exemplifying a relation between thermal conductivity of a mixture of gases and a mixture ratio of gases in the mixture of gases. The mixture of gases exemplified in FIG. 9 includes a gas A and a gas B. The mixture ratio of the gases may be referred to as a concentration of a gas. In FIG. 9, a vertical axis represents thermal conductivity, and a horizontal axis represents a mixture ratio of the gas A to the gas B in the mixture of gases. Because there is a difference in thermal conductivity between the gas A and the gas B, thermal conductivity of the mixture of gases changes according to the mixture ratio of the gas A to the gas B. That is, by measuring the thermal conductivity of the mixture of gases, the mixture ratio of the gas A to the gas B in the mixture of gases can be calculated. The thermal conductivity can be determined with the above (Mathematical formula 1) by the flow sensor 2 according to the embodiment obtaining ΔT. In the embodiment, for example, one of the gas A and the gas B is nitrogen, and another of the gas A and the gas B is argon mixed oxygen.

Figure 10A:
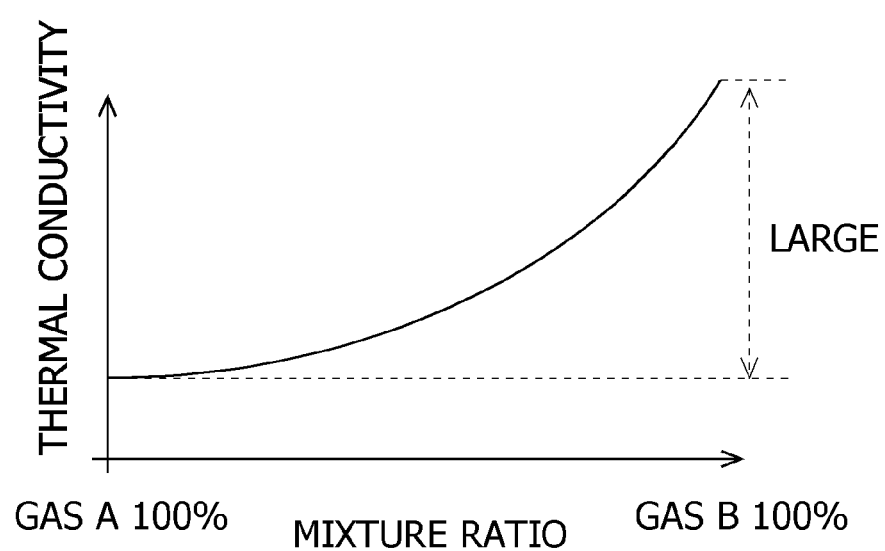
FIG. 10A is a first diagram comparing a relation between thermal conductivity of a mixture of gases and a mixture ratio of gases in the mixture of gases for each difference in thermal conductivity between a gas A and a gas B.
Figure 10B:
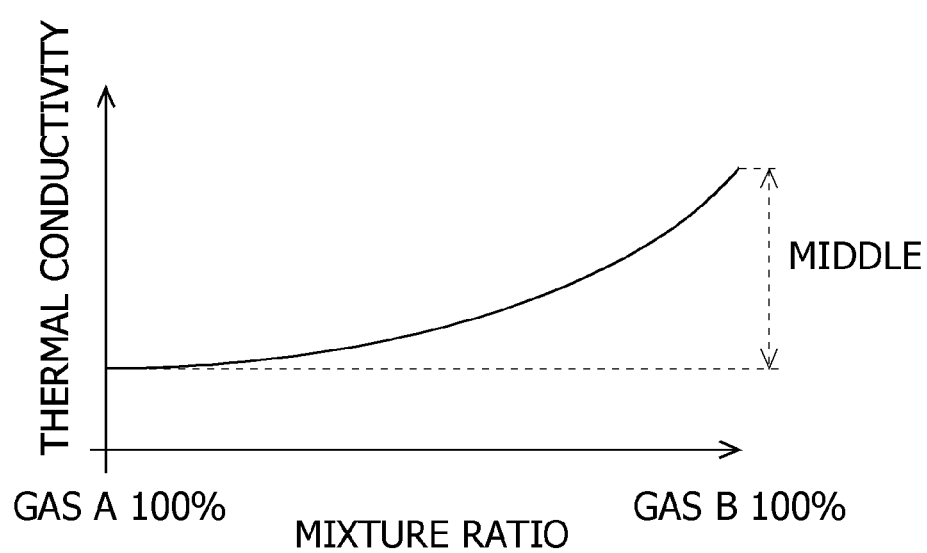
FIG. 10B is a second diagram comparing a relation between thermal conductivity of a mixture of gases and a mixture ratio of gases in the mixture of gases for each difference in thermal conductivity between a gas A and a gas B.
Figure 10C:
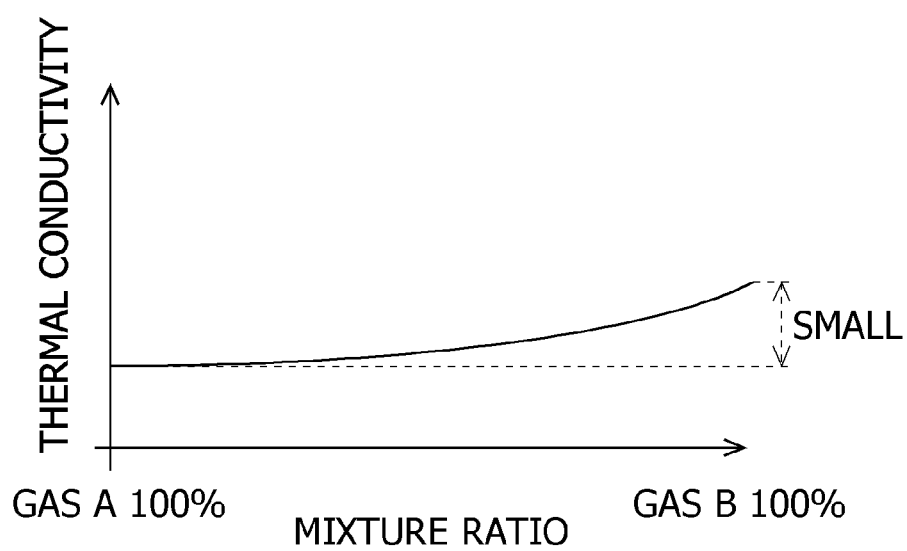
FIG. 10C is a third diagram comparing a relation between thermal conductivity of a mixture of gases and a mixture ratio of gases in the mixture of gases for each difference in thermal conductivity between a gas A and a gas B.

FIGS. 10A to 10C are diagrams comparing a relation between thermal conductivity of a mixture of gases and a mixture ratio of gases in the mixture of gases for each difference in thermal conductivity between a gas A and a gas B. In FIGS. 10A to 10C, as in FIG. 9, a vertical axis represents thermal conductivity, and a horizontal axis represents a mixture ratio of the gas A to the gas B in the mixture of gases including the gas A to the gas B. In FIGS. 10A to 10C, FIG. 10A exemplifies a state in which a difference in thermal conductivity between the gas A and the gas B is large, FIG. 10O illustrates a case in which the difference in thermal conductivity between the gas A and the gas B is small, and FIG. 10B illustrates a state in which the difference in thermal conductivity between the gas A and the gas B is in a middle of FIGS. 10A and 10C.

If the difference in thermal conductivity between the gas A and the gas B is large, as exemplified in FIG. 10A, the thermal conductivity of the mixture of gases including the gas A and the gas B markedly changes according to the mixture ratio of the gas A and the gas B. That is, a difference increases between the thermal conductivity of the mixture of gases including the gas A and the gas B in a state where the mixture ratio of the gas A is 100%, and the thermal conductivity of the mixture of gases including the gas A and the gas B in a state where the mixture ratio of the gas B is 100%. Then, as exemplified in FIGS. 10B and 10C, as the difference between the thermal conductivity of the gas A and the thermal conductivity of the gas B decreases, the difference between the thermal conductivity of the mixture of gases including the gas A and the gas B in a state where the mixture ratio of the gas A is 100%, and the thermal conductivity of the mixture of gases including the gas A and the gas B in a state where the mixture ratio of the gas B is 100% decreases. That is, it is preferable that a difference in thermal conductivity among gases in a mixture of gases be large in order to increase accuracy of calculating the mixture ratio of a certain gas in the mixture of gases on the basis of thermal conductivity.

Figure 11:
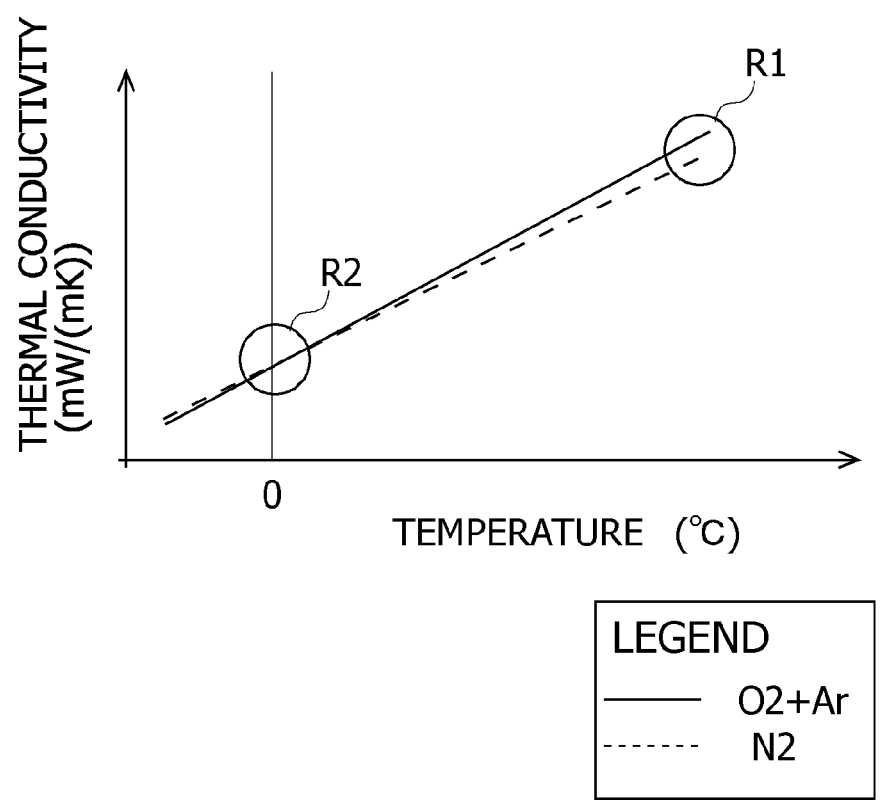
FIG. 11 is a diagram exemplifying thermal conductivity of argon mixed oxygen and thermal conductivity of nitrogen.

FIG. 11 is a diagram exemplifying thermal conductivity of argon mixed oxygen and thermal conductivity of nitrogen. In FIG. 11, a vertical axis represents thermal conductivity, and a horizontal axis represents temperature. That is, FIG. 11 exemplifies a change in thermal conductivity with respect to temperature. In the following drawings, argon mixed oxygen may be referred to as "O2+Ar" or "O2Ar". With reference to FIG. 11, it can be seen that a rate of change in thermal conductivity with respect to temperature is greatly different between argon mixed oxygen and nitrogen. Therefore, the difference in thermal conductivity between argon mixed oxygen and nitrogen is large in an area surrounded by a region R1 (high temperature region), while the difference in thermal conductivity between argon mixed oxygen and nitrogen is small in an area surrounded by a region R2 (low temperature region). Furthermore, in a range where temperature is higher than temperature of the region R2, thermal conductivity of argon mixed oxygen is higher than thermal conductivity of nitrogen, while in a range where temperature is equal to or lower than temperature of the region R2, thermal conductivity of argon mixed oxygen is lower than thermal conductivity of nitrogen. That is, in FIG. 11, there is a range in which the thermal conductivity of argon mixed oxygen and the thermal conductivity of nitrogen with respect to temperature intersect and are reversed.

That is, because a difference between thermal conductivity of argon mixed oxygen and thermal conductivity of nitrogen is large in the high temperature region, a mixing rate of argon mixed oxygen in a mixture of gases including argon mixed oxygen and nitrogen can be suitably calculated on the basis of thermal conductivity of the mixture of gases. Meanwhile, a difference between thermal conductivity of argon mixed oxygen and thermal conductivity of nitrogen is small in the low temperature region (or, the thermal conductivity of argon mixed oxygen and the thermal conductivity of nitrogen with respect to temperature intersect and are reversed). Therefore, a mixing rate of argon mixed oxygen in a mixture of gases including argon mixed oxygen and nitrogen is difficult to be calculated (calculation accuracy is decreased) on the basis of thermal conductivity of the mixture of gases.

Comparison of FIGS. 10A to 10C with FIG. 11 shows that it is only required to increase a difference between thermal conductivity of argon mixed oxygen and thermal conductivity of nitrogen by increasing temperature of a concentrated gas in order to increase accuracy of calculating a mixture ratio of argon mixed oxygen in a concentrated gas including argon mixed oxygen and nitrogen. The auxiliary memory 103 stores a correspondence between thermal conductivity in a concentrated gas and a mixture ratio of nitrogen to argon mixed oxygen for each temperature of the concentrated gas.

Figure 12:
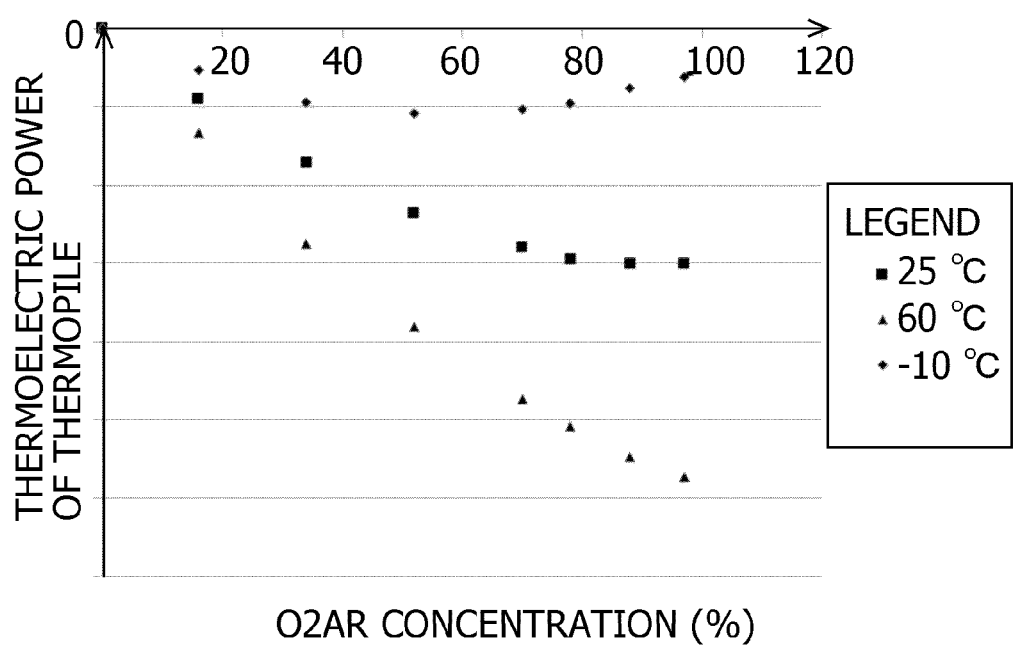
FIG. 12 is a diagram exemplifying a correspondence between an output value of a thermopile and a concentration of argon mixed oxygen with respect to the argon mixed oxygen.

A relation between thermal conductivity of a concentrated gas and a concentration of argon mixed oxygen will be further described. FIG. 12 is a diagram exemplifying a correspondence between an output value of a thermopile and a concentration of argon mixed oxygen with respect to the argon mixed oxygen. In FIG. 12, a vertical axis represents thermoelectric power of the thermopile 24, and a horizontal axis represents the concentration of argon mixed oxygen. FIG. 12 exemplifies a case where temperature of a concentrated gas is 60° C., 25° C., and minus 10° C.

With reference to FIG. 12, it can be seen that an output value of the thermopile 24 and the concentration of argon mixed oxygen are corresponding on a one-to-one basis, in a case where temperature of the concentrated gas is 60° C. Therefore, in a case of 60° C., concentration of argon mixed oxygen can be uniquely determined on the basis of the output value of the thermopile 24. However, in a case where the temperature of the concentrated gas is 25° C., the one-to-one relation between the output value of the thermopile 24 and the concentration of argon mixed oxygen starts to collapse around when the concentration of argon mixed oxygen exceeds 80%. Further, in a case where the temperature of the concentrated gas is minus 10° C., the one-to-one relation between the output value of the thermopile 24 and the concentration of argon mixed oxygen starts to collapse around when the concentration of argon mixed oxygen exceeds 50%. In a range in which the one-to-one relation between the output value of the thermopile 24 and the concentration of argon mixed oxygen collapses, the concentration of argon mixed oxygen cannot be uniquely determined on the basis of the output value of the thermopile 24. Therefore, accuracy of measuring the concentration of argon mixed oxygen with the flow sensor 2 is decreased, or the accuracy cannot be measured.

Figure 13:
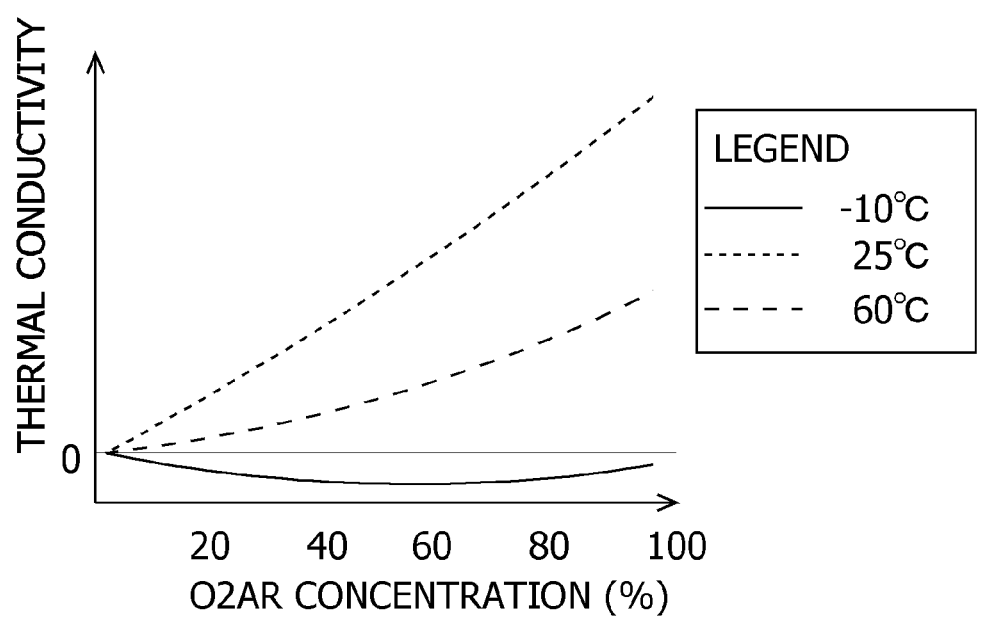
FIG. 13 is a diagram exemplifying a relation between the concentration of argon mixed oxygen and thermal conductivity of a concentrated gas.

FIG. 13 is a diagram exemplifying a relation between the concentration of argon mixed oxygen and thermal conductivity of a concentrated gas. In FIG. 13, a vertical axis represents thermal conductivity, and a horizontal axis represents the concentration of argon mixed oxygen. FIG. 13 exemplifies a simulation result of a relation between the concentration of argon mixed oxygen and the thermal conductivity. As can be seen with reference to FIG. 13, a relation between the thermal conductivity of a concentrated gas and the concentration of argon mixed oxygen forms a quadratic curve. This is considered to be because efficiency of thermal conductance between different kinds of molecules in a mixture of gases is lower than thermal conductivity between the same kind of molecules. In the quadratic curve, increase and decrease of the concentration are reversed across a vertex. Therefore, two values indicating concentrations correspond to one value indicating thermal conductivity.

With reference to FIG. 13, it can be seen that a position of the vertex of the quadratic curve varies according variation in temperature of the concentrated gas. For example, in FIG. 13, in a case where the temperature is minus 10° C., the thermal conductivity of the concentrated gas is substantially equal in a case where the concentration of argon mixed gas is 80% and in a case where the concentration of argon mixed gas is 40%. If one of the values indicating two concentrations is out of a measurement range (for example, out of a range of 0% or more and 100% or less, the range being a variance range of a value indicating a concentration), an accurate concentration can be measured by discarding the value. That is, if the position of the vertex is set outside the range for which a concentration is measured, a correspondence between the thermal conductivity and the concentration in the range for which the concentration is measured can be on a one-to-one basis. Furthermore, with reference to FIG. 13, it can be seen that the range in which the relation between the thermal conductivity and the concentration of the mixture of gases is not on a one-to-one basis increases as the temperature of the concentrated gas decreases, and the range in which the relation between the thermal conductivity and the concentration of argon mixed oxygen is on a one-to-one basis increases as the temperature of the concentrated gas increases.

Figure 14:
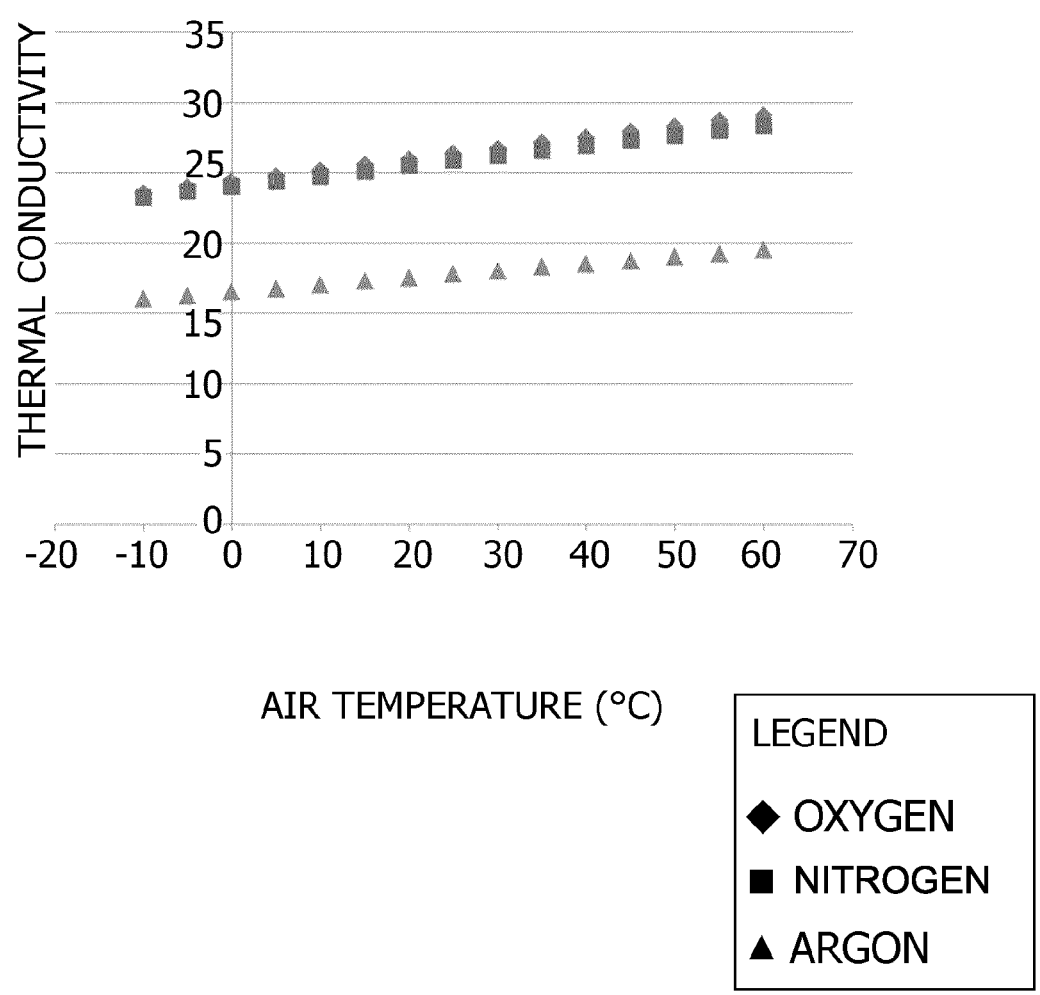
FIG. 14 is a diagram exemplifying a relation between air temperature and thermal conductivity for each of three kinds of gases that are oxygen, nitrogen, and argon.

FIG. 14 is a diagram exemplifying a relation between air temperature and thermal conductivity for each of three kinds of gases that are oxygen, nitrogen, and argon. In FIG. 14, a vertical axis represents thermal conductivity, and a horizontal axis represents air temperature. With reference to FIG. 14, it can be seen that, because thermal conductivity of argon is very low as compared to thermal conductivity of nitrogen and oxygen, a difference in thermal conductivity between oxygen and nitrogen decreases due to mixing of argon even in a small amount.

Because a concentrated gas generated by the oxygen concentrator is a mixture of gases including oxygen and a trace amount of argon as described above, the flow sensor 2 according to the embodiment preferably increases accuracy of measuring the concentration of argon mixed oxygen, which is a mixture of gases, in the concentrated gas.

Figure 15:
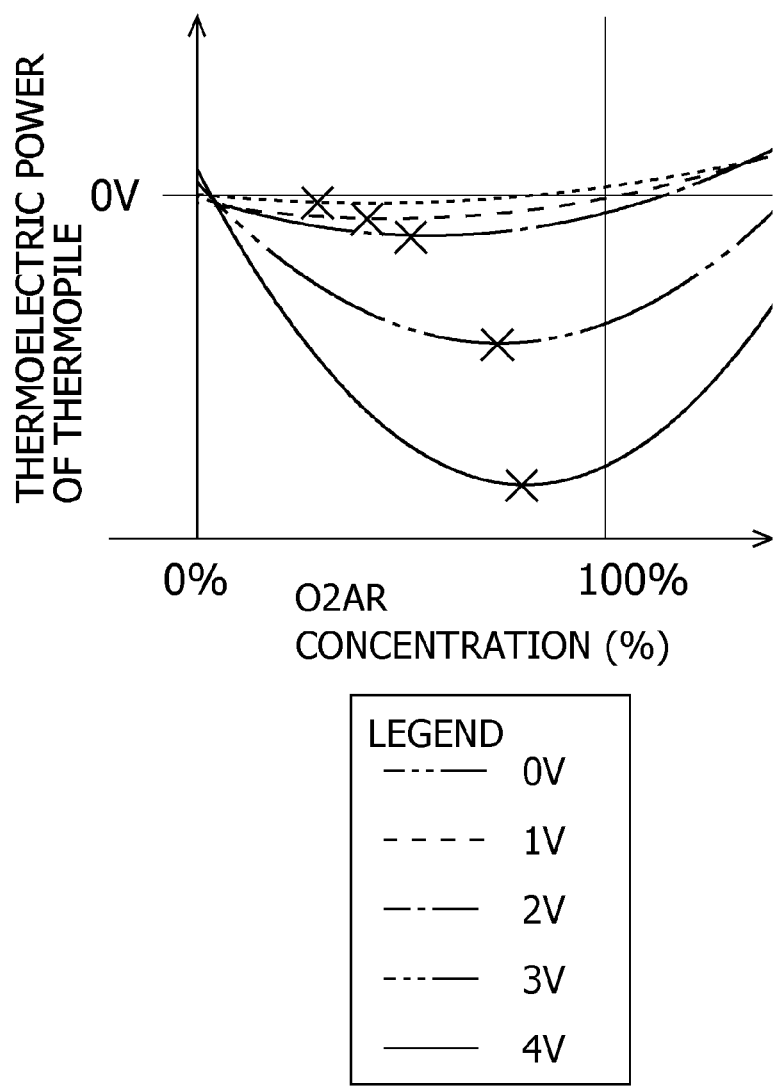
FIG. 15 is a diagram exemplifying a relation between the concentration of argon mixed oxygen and an output value of the thermopile included in the flow sensor according to the embodiment in a case where a voltage applied to a heater is changed.

FIG. 15 is a diagram exemplifying a relation between a concentration of argon mixed oxygen and an output value of the thermopile included in the flow sensor according to the embodiment in a case where a voltage applied to a heater is changed. In FIG. 15, a vertical axis represents thermoelectric power (output value) of the thermopile 24, and a horizontal axis represents the concentration of argon mixed oxygen.

FIG. 15 exemplifies a position of a vertex of each of quadratic curves with an "x". Each of the quadratic curves indicates a quadratically changing relation between the concentration of argon mixed oxygen and an output value of the thermopile included in the flow sensor according to the embodiment.

As can be seen with reference to FIG. 15, as a voltage applied to the heater 23 is increased to 0V, 1V, 2V, 3V, and 4V, the position of the vertex of a quadratic curve moves to a position where the output value of the thermopile 24 is low in the vertical axis direction, and moves in a direction indicating the concentration of 100% in the horizontal axis direction. As a result, as the voltage applied to the heater 23 increases, the range in which the output value of the thermopile 24 and the concentration of argon mixed oxygen correspond to each other on a one-to-one basis increases. This is considered to be because temperature of air near the thermopile 24 increases by increasing the voltage applied to the heater 23.

Figure 16:
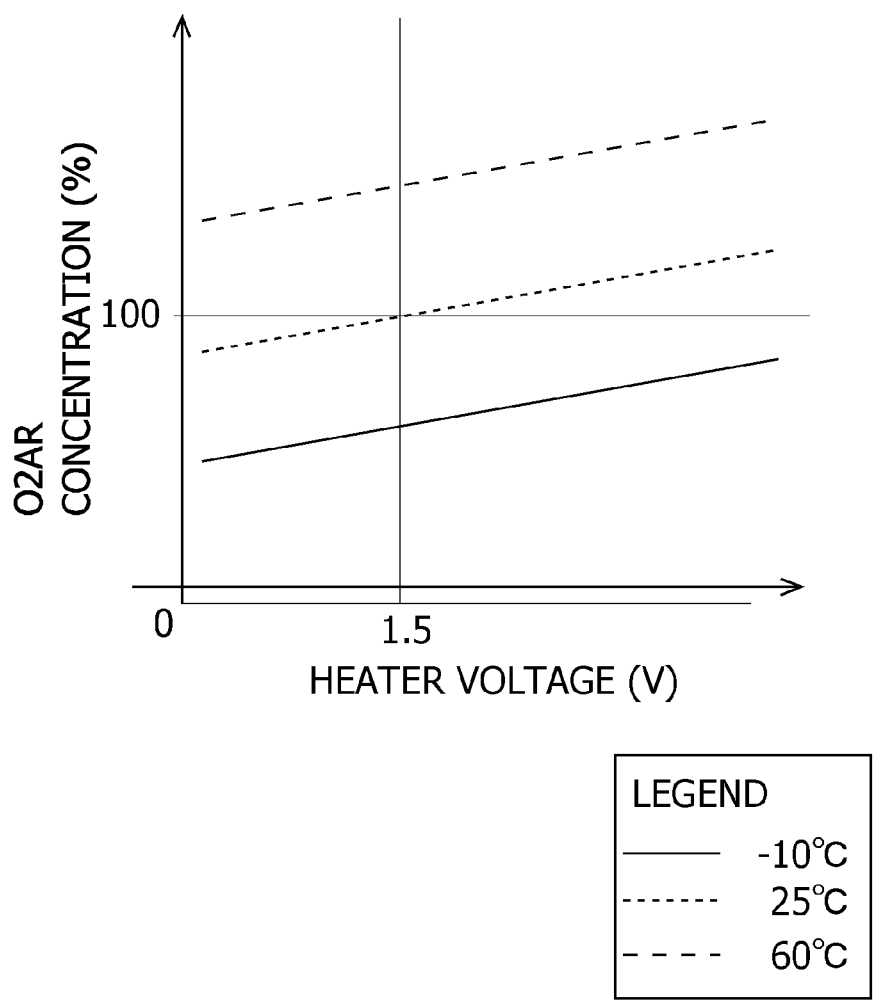
FIG. 16 is a diagram schematically illustrating an example of the relation between the concentration of argon mixed oxygen and the voltage applied to the heater, at a vertex position of quadratic curves exemplified in FIG. 15.

FIG. 16 is a diagram schematically illustrating an example of a relation, at a vertex position of the quadratic curves, between a concentration of argon mixed oxygen and a voltage applied to the heater, the example being exemplified in FIG. 15. In FIG. 16, a vertical axis represents the concentration of argon mixed oxygen, and a horizontal axis represents the voltage applied to the heater 23. FIG. 16 exemplifies a case where temperature of the mixture of gases is 60° C., 25° C., and minus 10° C.

With reference to FIG. 16, it can be seen that the concentration at a position of a vertex of the quadratic curves is substantially proportional to the voltage applied to the heater 23 in each of the cases of 60° C., 25° C., and minus 10° C. Furthermore, with reference to FIG. 16, it can be seen that the concentration of argon mixed oxygen at the vertex position of a quadratic curve increases as the voltage applied to the heater 23 increases. In FIG. 16, for example, when the voltage applied to the heater 23 is set to 1.5 V, the concentration at the position of the vertex is 60% in a case where the temperature of the mixture of gases is minus 10° C., and the concentration at the position of the vertex is 100% in a case where the temperature of the mixture of gases is 25° C. That is, as a result of the movement of vertex of the quadratic curve by an increase in the temperature of the concentrated gas including argon mixed oxygen and nitrogen, a difference in thermal conductivity between nitrogen and argon mixed gas can be increased in the region R1 that is a high temperature region as described with reference to FIGS. 10A to 10C, by which accuracy of measuring a mixture ratio (concentration) of the argon mixed oxygen by the flow sensor 2 can be increased.

Figure 17:
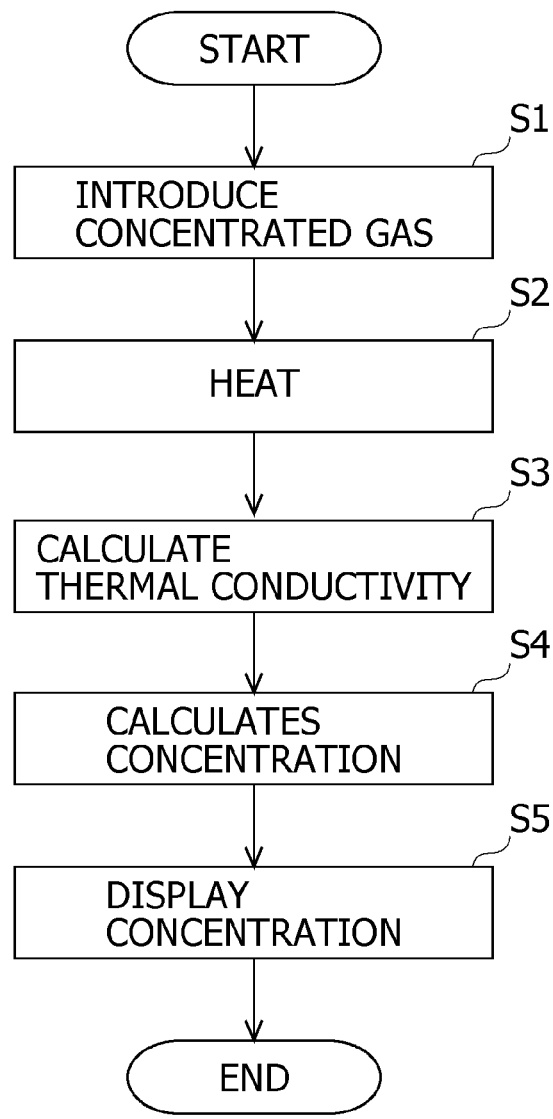
FIG. 17 is a diagram illustrating an example of a processing flow of the flow sensor according to the embodiment.

FIG. 17 is a diagram illustrating an example of a processing flow of the flow sensor according to the embodiment. In a processing flow exemplified in FIG. 17, the flow sensor 2 measures a concentration of argon mixed oxygen in a concentrated gas concentrated by the oxygen concentrator 200. Hereinafter, an example of a processing flow of the flow sensor 2 according to the embodiment will be described with reference to FIG. 17.

In Step S1, the concentrated gas generated by the oxygen concentrator 200 is introduced into near a thermopile 24 of the flow sensor 2. In Step S2, the controller 100 applies a voltage to the heater 23 to cause the heater 23 to generate heat. The concentrated gas introduced into near the thermopile 24 is heated by heat from the heater 23.

In Step S3, the controller 100 acquires thermoelectric power in the thermopile 24. The controller 100 determines ΔT on the basis of a correspondence between the thermoelectric power and ΔT, the correspondence being stored in the auxiliary memory 103. Furthermore, from the auxiliary memory 103, the controller 100 acquires thermal resistance $R_t$ of the thermopile 24 and an amount of heat generated by the heater 23, the amount of heat corresponding to the voltage applied in Step S2. The controller 100 calculates thermal resistance of the concentrated gas by applying the thermal resistance of the thermopile and the amount of heat generated by the heater 23, which are acquired from the auxiliary memory 103, to (Mathematical formula 1) stored in the auxiliary memory 103.

In Step S4, the controller 100 calculates the concentration of argon mixed oxygen in the concentrated gas on the basis of the thermal resistance calculated in Step S3. The controller 100 calculates thermal conductivity of the concentrated gas on the basis of the thermal resistance of the concentrated gas calculated in Step S3. The controller 100 refers to a correspondence between the thermal conductivity of the concentrated gas stored in the auxiliary memory 103 and the mixture ratio of nitrogen and argon mixed oxygen, and determines the mixture ratio (concentration) of argon mixed oxygen. In Step S5, the controller 100 causes the display 104 to display the concentration of argon mixed oxygen determined in Step S4.

(Function and Effect of Flow Sensor)

As described with reference to FIGS. 12 and 13, a one-to-one relation between the concentration of argon mixed oxygen and the thermal conductivity collapses in a low temperature region (for example, near minus 10° C.). By the controller 100 increasing voltage applied to the heater 23, the flow sensor 2 according to the embodiment can increase a range in which the output value of the thermopile 24 and the concentration of argon mixed oxygen correspond on a one-to-one basis.

In the flow sensor 2 according to the embodiment, when the flow sensor 2 measures the concentration of argon mixed oxygen, the controller 100 applies, to the heater 23, the second voltage higher than the first voltage that is applied to the heater 23 when measuring a flow rate or a flow velocity of fluid. By increasing a voltage applied to the heater 23, accuracy of measuring the concentration of argon mixed oxygen is increased. That is, concentration measurement accuracy can be increased also for argon mixed oxygen that is greatly different from nitrogen in a rate of change in thermal conductivity with respect to temperature. Such an effect is also effective in a case where a low-temperature concentrated gas is supplied to the flow sensor 2.

<Modifications>

Figure 18:
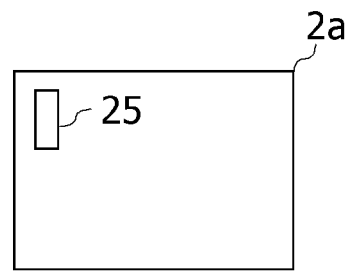
FIG. 18 is a diagram illustrating an example of a flow sensor including a thermometer.

The flow sensor 2 according to the embodiment may include a thermometer that measures temperature of a concentrated gas. FIG. 18 is a diagram illustrating an example of a flow sensor including a thermometer. A flow sensor 2a exemplified in FIG. 18 includes a thermometer 25 that measures temperature of a concentrated gas. A position where the thermometer 25 is provided is not particularly limited as long as the position is where temperature of a concentrated gas can be measured.

The flow sensor 2a stores, in the auxiliary memory 103 of the controller 100, a concentration-voltage relation, a vertex position of the quadratic curves, between a concentration of argon mixed oxygen and a voltage applied to the heater 23, as exemplified in FIG. 16. That is, the auxiliary memory 103 can store a correspondence between a range in which the concentration of a mixture of gases can be uniquely determined on the basis of the output value (thermoelectric power) of the thermopile 24 and a voltage of the heater 23 for each voltage applied to the heater 23. A data format for storing a concentration-voltage relation in the auxiliary memory 103 is not particularly limited. The auxiliary memory 103 may store the concentration-voltage relation in a form of a function, a table, or the like, for example. With such a configuration, when acquiring air temperature from the thermometer 25, the controller 100 can determine, with reference to the concentration-voltage relation stored in the auxiliary memory 103, voltage that enables measurement of the concentration of argon mixed oxygen, and can apply the determined voltage to the heater 23.

Figure 19:
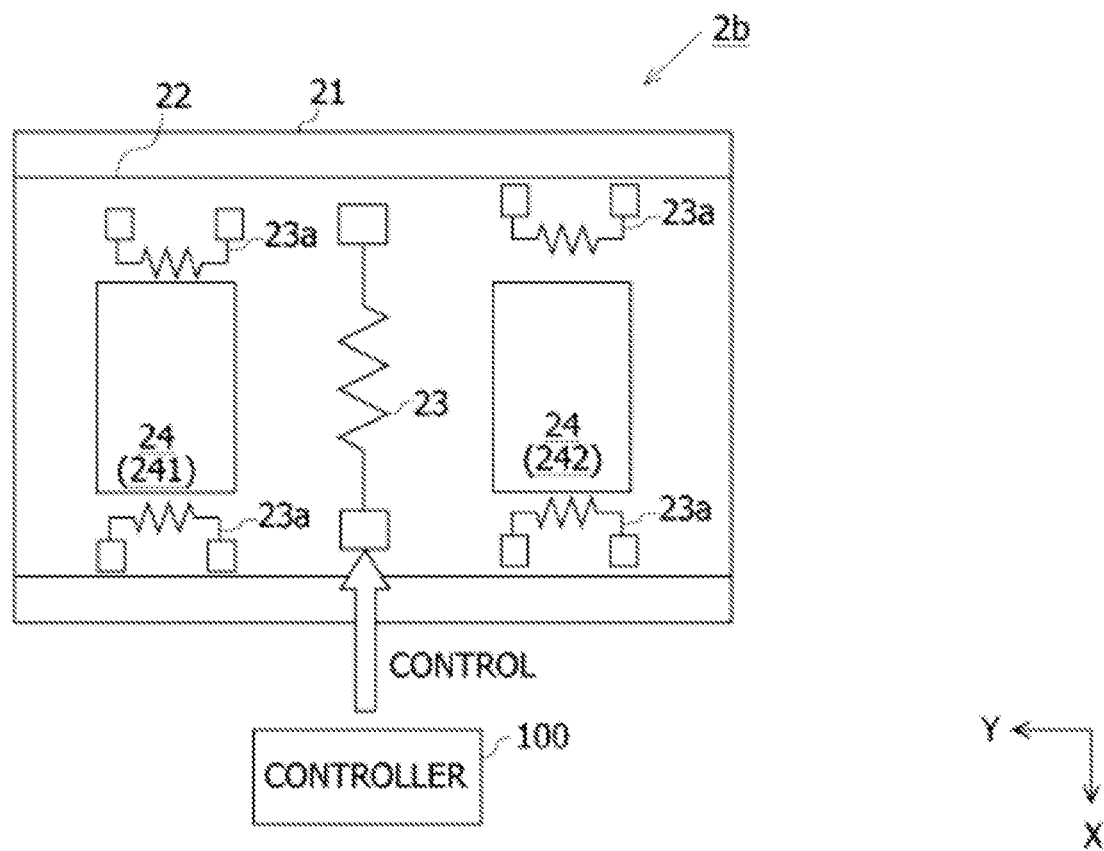
FIG. 19 is a diagram illustrating an example of a flow sensor including a heater that heats a concentrated gas near thermopiles.

In the embodiment, the heater 23 used for heating the membrane 22 is also used for heating a concentrated gas. However, the flow sensor may separately include a heater that heats a concentrated gas near the thermopiles 24, 24. FIG. 19 is a diagram illustrating an example of a flow sensor including a heater that heats a concentrated gas near thermopiles. FIG. 19 is a top view of a flow sensor 2b. The flow sensor 2b exemplified in FIG. 19 includes a heater 23a near each of the thermopiles 24, 24.

With such a configuration also, concentrated gas near the thermopiles 24, 24 can be heated, and therefore, accuracy of measuring the concentration of argon mixed oxygen can be increased. Furthermore, by arranging the heater 23 and the heater 23a on a flow sensor manufactured by an MEMS, the heater 23 and the heater 23a can be simultaneously formed, and therefore, a manufacturing cost can be reduced. Furthermore, because the heater 23 and the heater 23a are arranged on the same MEMS flow sensor, downsizing of the flow sensor is facilitated.

Figure 20:
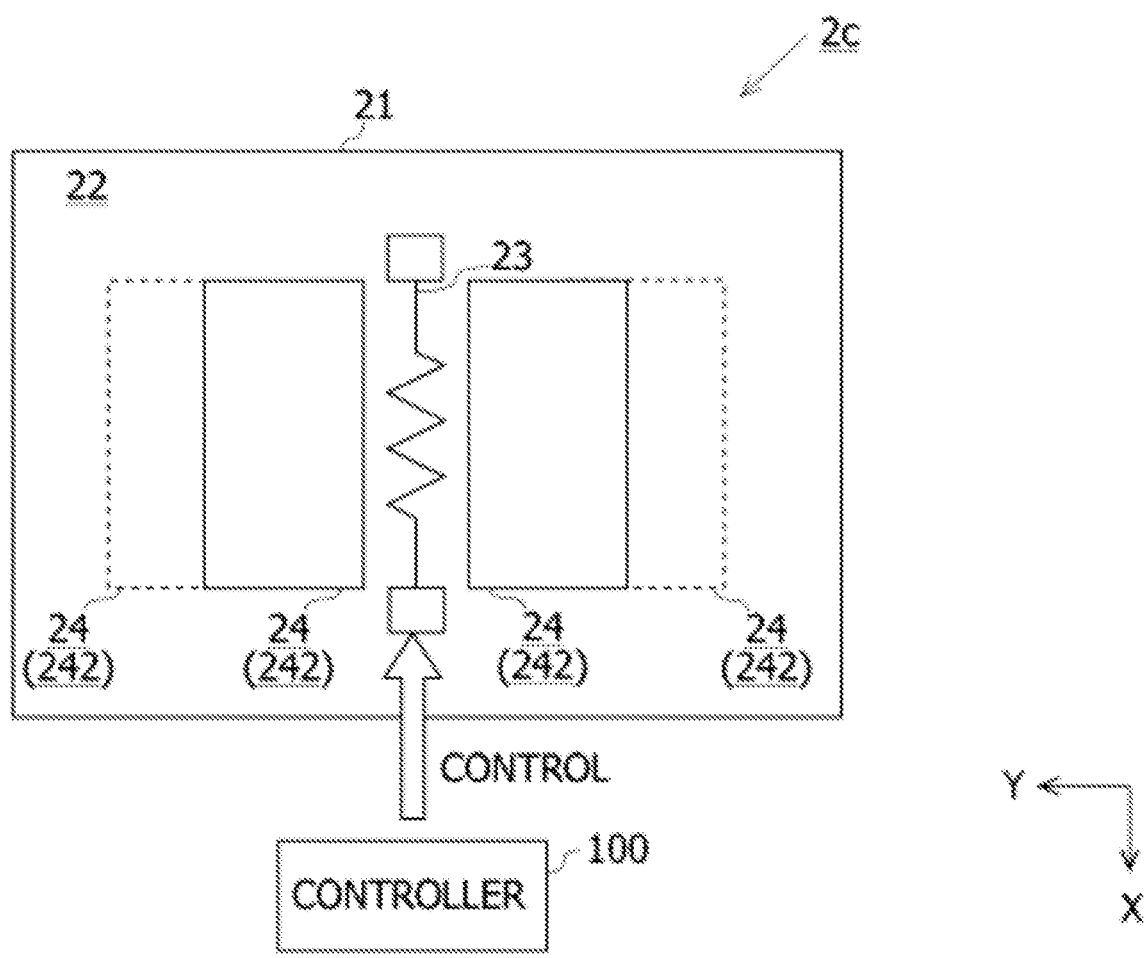
FIG. 20 is a diagram illustrating an example of a flow sensor in which thermopiles are arranged at a position closer to a heater as compared to the embodiment.

The thermopiles 24, 24 may be arranged at positions closer to the heater 23 as compared to the flow sensor 2 according to the embodiment. FIG. 20 is a diagram illustrating an example of a flow sensor in which thermopiles are arranged at a position closer to a heater as compared to the embodiment. FIG. 20 is a top view of a flow sensor 2c. In FIG. 20, positions of the thermopiles 24 in the flow sensor 2 according to the embodiment exemplified in FIG. 1 are exemplified by dotted lines. In the flow sensor 2c exemplified in FIG. 20, the thermopiles 24, 24 are arranged at positions closer to the heater 23 as compared to the flow sensor 2 according to the embodiment. By arranging the thermopiles 24, 24 at such positions, a concentrated gas near the thermopiles 24, 24 can be heated by the heater 23 more efficiently than in the embodiment.

In the above description, the flow sensor 2 is applied to measurement of the concentration of argon mixed oxygen. However, the flow sensor 2 can also be applied to measurement of the concentration of a gas other than argon mixed oxygen. Hereinafter, as an example, a mode in which the flow sensor 2 is applied to measurement of a concentration of hydrogen mixed in a fuel gas exemplified by LP gas and city gas will be described. Main components of LP gas are propane and butane, and a main component of city gas is methane. Hydrogen may be mixed into a fuel gas in order to reduce carbon dioxide generated when the fuel gas is combusted or to use the fuel gas as a supply source of hydrogen used for a fuel cell.

Figure 21:
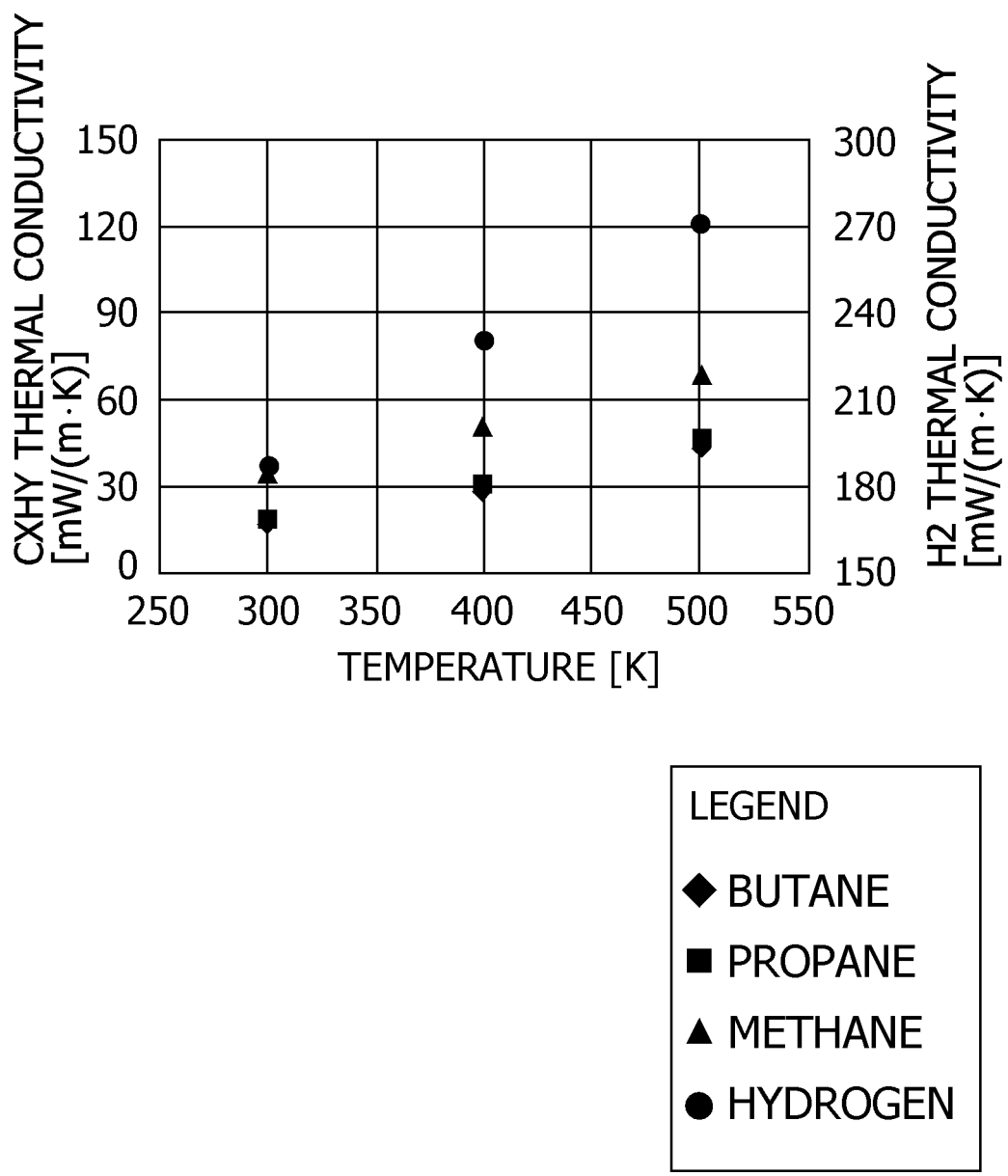
FIG. 21 is a diagram exemplifying a relation between temperature and thermal conductivity for each of four kinds of gases that are butane, propane, methane, and hydrogen.

FIG. 21 is a diagram exemplifying a relation between temperature and thermal conductivity for each of four kinds of gases that are butane, propane, methane, and hydrogen. In FIG. 21, the horizontal axis represents temperature of gas. Furthermore, in FIG. 21, a vertical axis on a left side represents thermal conductivity of butane, propane, and methane (hereinafter, collectively referred to as CxHy), and a vertical axis on a right side represents thermal conductivity of hydrogen. With reference to FIG. 21, it can be seen that, when a mixture of gases including CxHy and hydrogen is heated, a difference in thermal conductivity between CxHy and hydrogen increases. That is, by heating the mixture of gases including CxHy and hydrogen, thermal conductivity and the concentration of hydrogen concentration can be associated with each other on a one-to-one basis.

The flow sensor 2 according to the embodiment can be applied to measurement of a concentration of hydrogen by setting temperature of the mixture of gases including CxHy and hydrogen by heating so that the temperature falls within a range in which the concentration of hydrogen can be uniquely determined with respect to thermal conductivity. Thus, the flow sensor 2 according to the embodiment can be applied to measurement of a concentration of various measurement target gases by heating a mixture of gases so that temperature of the mixture of gases is set to fall within a range in which the concentration of the measurement target gas can be uniquely determined with respect to thermal conductivity.

In the embodiment and the modifications described above, a thermal flow sensor using a thermopile 24 has been described as an example of a flow sensor. However, the disclosed technology is not limited to a thermal flow sensor. The disclosed technology can also be applied to a flow sensor other than a thermal flow sensor, for example, as long as an output value varies according to thermal conductivity (or thermal resistivity) of fluid. Examples of such a sensor include a resistance temperature detector, a radiation thermometer, and the like. Furthermore, examples of the radiation thermometer include a bolometer, a pyroelectric sensor, and the like.

The controller 100 may control a voltage applied to the heater 23 so that an amount of heat generated by the heater 23 is constant. Variation in temperature of a concentrated gas near the thermopiles 24, 24 is reduced (maintained constant) by heat generation amount being controlled by the heater 23 in this way. Therefore, influence of a surrounding environment on thermoelectric power output from the thermopiles 24, 24 is reduced. Therefore, calibration at a time of measurement of a concentration can be simplified or omitted. Furthermore, life of the heater 23 can be expected to be prolonged.

In the flow sensor 2 according to the embodiment, power may be supplied to the heater 23 when the oxygen concentrator 200 is generating a concentrated gas, and power supply to the heater 23 may be stopped when the oxygen concentrator 200 is not generating a concentrated gas. By adopting such a configuration, power of the flow sensor 2 is saved, and the life of the heater 23 can be expected to be prolonged.

The flow sensor 2 according to the embodiment measures a concentration of argon mixed oxygen in a concentrated gas concentrated by the oxygen concentrator 200. However, a target of measurement by the flow sensor 2 is not limited to argon mixed oxygen in a concentrated gas. The flow sensor 2 may measure a concentration of a predetermined component in a mixture of gases including a plurality of gases.

The flow sensor 2 according to the embodiment includes two thermopiles 24. However, one thermopile 24 is sufficient as long as the concentration of argon mixed oxygen is measured without measurement of a flow velocity or a flow rate of fluid.

<Supplementary Note 1>
A concentration measurement device (2) including a sensor (2, 22, 23, 24) configured to measure a concentration of a measurement target gas (oxygen, argon, hydrogen) in a mixture of gases on the basis of thermal conductivity of the measurement target gas, the mixture of gases including two or more components, and a heating unit (23) configured to heat the mixture of gases so that the concentration of the measurement target gas can be uniquely determined with respect to the thermal conductivity.

<Supplementary Note 2>
A concentration measurement device (2) configured to be applied to a concentrator (200) configured to generate a concentrated gas in which a concentration of two or more predetermined components (oxygen, argon) in air is increased, including a sensor (2, 22, 23, 24) configured to measure a concentration of a mixture of gases in a mixture of gases including the two or more predetermined components in the concentrated gas on the basis of thermal conductivity of the mixture of gases, and a heating unit (23) configured to heat the mixture of gases so that the concentration of the mixture of gases can be uniquely determined with respect to the thermal conductivity.

The above-described embodiment and modifications can be combined with each other.

DESCRIPTION OF SYMBOLS 2, 2a, 2b, 2c flow sensor
21 main body
22 membrane
23, 23a heater
24, 241, 242 thermopile
24a one end
24b another end
25 thermometer
100 controller
101 CPU
102 main memory
103 auxiliary memory
200 oxygen concentrator

The invention claimed is:
1. A concentration measurement device comprising:
a sensor configured to measure a concentration of a measurement target gas in a mixture of gases on the basis of thermal conductivity of the measurement target gas, the mixture of gases including two or more components; and
a heating unit configured to heat the mixture of gases so that the concentration of the measurement target gas can be uniquely determined with respect to the thermal conductivity,
wherein:
the sensor includes a pair of thermoelectromotive devices in which electromotive force according to temperature is generated and a heating unit that is placed between the pair of thermoelectromotive devices and that generates heat according to an applied voltage, and measures a flow rate of the mixture of gases according to the electromotive force generated in the pair of thermoelectromotive devices heated by the heating unit,
the concentration measurement device further includes a controller configured to control a voltage applied to the heating unit, and
the controller applies, to the heating unit, a second voltage higher than a first voltage that is applied when mea- suring a flow rate of the mixture of gases, and causes the sensor to measure a concentration of the measurement target gas.

2. The concentration measurement device according to claim 1, the concentration measurement device further comprising a thermometer configured to measure temperature of the mixture of gases, wherein the controller stores, for each temperature of the mixture of gases, a correspondence between a range in which the concentration of the measurement target gas can be uniquely determined on the basis of electromotive force generated in the thermoelectromotive device and a voltage applied to the heating unit, and the controller acquires temperature of the mixture of gases measured by the thermometer and determines the second voltage by referring to the correspondence on the basis of the acquired temperature.

3. The concentration measurement device according to claim 1, the concentration measurement device being configured to be applied to a concentrator configured to generate a concentrated gas in which concentrations of two or more predetermined components in air are increased, wherein the mixture of gases is a concentrated gas concentrated by the concentrator, and the measurement target gas is a gas including the two or more predetermined components included in the concentrated gas.

4. The concentration measurement device according to claim 3, wherein the concentrator removes nitrogen from air including nitrogen, oxygen, and argon to generate a concentrated gas in which concentrations of oxygen and argon are increased, the predetermined component includes oxygen and argon, and the sensor is provided on a flow path through which the concentrator supplies the concentrated gas.

* * * * *